United States Patent [19]

Reiter et al.

[11] Patent Number: 5,478,825
[45] Date of Patent: Dec. 26, 1995

[54] 5-(SUBSTITUTED AMINO)-1,2,4-TRIAZOLO (1,5-A) PYRIMIDINE DERIVATIVES

[75] Inventors: József Reiter, Budapest; Gábor Berecz, Nagyőrös; Gizella Zsila, Budapest; Lujza Peőcz, Budapest; Gábor Gigler, Budapest; Márton Fekete, Budapest; Mária Szécsey née Hegeűs, Budapest; EniőSzirt née Kiszelly, Budapest; Ludmila Rohács née Zamkovaja, Budapest; Frigyes Görgényi, Budapest; Margit Csörő, Budapest, all of Hungary

[73] Assignee: Egis Gyogyszergyar, Budapest, Hungary

[21] Appl. No.: 261,214

[22] Filed: Jun. 15, 1994

Related U.S. Application Data

[63] Continuation of Ser. No. 993,442, Dec. 17, 1992, abandoned, which is a continuation-in-part of Ser. No. 839,505, Feb. 21, 1992, abandoned.

[30] Foreign Application Priority Data

Feb. 22, 1991 [HU] Hungary ..................... 587/91

[51] Int. Cl.$^6$ .................... A61K 31/535; A61K 31/505; C07D 471/14
[52] U.S. Cl. .............. 514/233.2; 514/253; 514/257; 514/232.5; 544/81; 544/115; 544/118; 544/251; 544/263; 544/357; 544/80
[58] Field of Search ............ 514/115, 118, 514/233.2, 232.5, 253, 257; 544/81, 251, 80

[56] References Cited

U.S. PATENT DOCUMENTS

| | | | |
|---|---|---|---|
| 4,036,840 | 7/1977 | O'Brien et al. | 544/263 |
| 4,127,655 | 11/1978 | Denzel et al. | 544/115 |
| 4,169,948 | 10/1979 | Dunbar et al. | 544/118 |
| 4,497,814 | 2/1985 | Witkowski | 544/263 |
| 4,617,303 | 10/1986 | Eiken et al. | 544/303 |
| 4,831,029 | 5/1989 | Reiter et al. | 514/267 |
| 5,064,826 | 11/1991 | Reiter et al. | 514/267 |

FOREIGN PATENT DOCUMENTS

| | | | |
|---|---|---|---|
| 0642073 | 8/1992 | Australia | 544/263 |
| 0283623 | 10/1990 | Germany | 544/263 |
| 208693 | 8/1993 | Hungary . | |
| 1423266 | 7/1979 | United Kingdom . | |
| 1148629 | 11/1979 | United Kingdom . | |
| 280111 | 6/1990 | United Kingdom . | |

OTHER PUBLICATIONS

Reiter, J. Het. Chem, vol. 28 pp. 721–729 (1991).
Reiter, Org. Prep. Proced, vol. 21 pp. 163–171 (1989).
Reiter, J., et al., "On Triazoles. VIII[1]. The Reaction of 5-Amino-1,2,4-Triazoles with Ethyl 2-Cyano-3-Ethoxyacrylate and 2-Cyano-3-Ethoxyacrylonitrile [2]", Journal of Heterocyclic Chemistry (1987), vol. 24, pp. 1149–1154.
Ram, V., "Chemotherapeutic Agents: Part XII–Synthesis of 2–Pyridyl-1,2,4–triazolo[1,5–1]pyrimidines as antimicrobial agent", Indian Journal of Chemistry (1989), vol. 28B, pp. 242–246.
Chemical Abstracts (1991), vol. 114, p. 693, abstract number 62114w.
Wu, M. T., et al., "Annelated piperazinly-7, 8–dihydro–6H–thiopyranol [3,2-d]pyrimidines", Journal of Heterocyclic Chemistry (1990), vol. 27, pp. 1559–1563.
Ram, V., "Chemotherapeutic Agents: Part X–Synthesis of 2–Pyridyl [1,2,4]triazolo–[1,5–a]pyrimidines as Leishmanicides", Indian Journal of Chemistry (1988), vol. 27B, pp. 825–829.
Chemical Abstracts (1989), vol. 110, p. 747, abstract number 212752m.

*Primary Examiner*—Donald G. Daus
*Attorney, Agent, or Firm*—Beveridge, DeGrandi, Weilacher & Young

[57] ABSTRACT

The disclosed compounds have the formula $$\begin{array}{c} R^1 \\ R^2 \end{array} \begin{array}{c} Z \\ N \end{array} \begin{array}{c} N-N \\ N \end{array} Q$$

wherein

Q is a 6-membered saturated heterocyclic group or a group S(O)pR$^3$, wherein p is 0, 1, or 2, and R$^3$ is alkyl, alkenyl, or phenyl-, which may have halogen or nitro substituents, or phenyl optionally substituted; or NR$^4$R$^5$ wherein R$^4$ and R$^5$ are hydrogen, alkyl, alkenyl, phenyl-alkyl, or di-alkyl-amino-alkyl;

R$^1$ and R$^2$ are hydrogen or alkyl, or together form a group (CH$_2$)n—Y—(CH$_2$)m, wherein Y is CH$_2$, or NR$^6$, wherein R$^6$ is phenyl-alkyl, n and m are 0 or 1 to 5;

Z is NR$^7$R$^8$, wherein

R$^7$ and R$^8$ each are hydrogen, alkenyl, cycloalkyl, adamantayl, or phenyl-alkyl, which may have one or more substituents or together form a group of (CH$_2$)j—W—(CH$_2$)k, wherein j and k each are 1 to 3, and W is oxygen, CH$_2$, CHOH, or NR$^{10}$, wherein R$^{10}$ is hydrogen, alkoxycarbonyl, or alkyl, which latter may be substituted.

or SR$^9$, wherein

R$^9$ is alkyl substituted by alkoxy-carbonyl and possess inotropic and antianginal effects, complemented by antiinflammatory, ulcus, and gastric acid secretion inhibiting, and by weaker tranquillant, spasmolytic, and analgesic properties.

5 Claims, No Drawings

5-(SUBSTITUTED AMINO)-1,2,4-TRIAZOLO (1,5-A) PYRIMIDINE DERIVATIVES

This application is a continuation of application Ser. No. 07/993,442, filed Dec. 17, 1992 abandoned, which application is entirely incorporated herein by reference, which application is a continuation-in-part of application Ser. No. 07/839,505, filed Feb. 21, 1992 abandoned, which application is entirely incorporated herein by reference.

This invention relates to new 1,2,4-triazolo[1,5-a]pyrimidine derivatives, a process for the preparation thereof, pharmaceutical compositions comprising the same, to the use of the said 1,2,4-triazolo[1,5-a]pyrimidine derivatives for the treatment of diseases and for the preparation of pharmaceutical compositions suitable for the treatment of diseases.

According to an aspect of the present invention there are provided new 1,2,4-triazolo[1,5-a]pyrimidine derivatives of the general Formula (I)

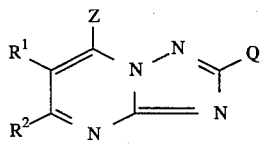

and pharmaceutically acceptable acid addition salts thereof, wherein

Q represents a 6-membered saturated heterocyclic group containing one or more nitrogen and/or oxygen atom(s) which group is bonded to the triazole ring by the heterocyclic nitrogen atom and optionally carrying a $C_{1-4}$ alkyl substituent, or a group of the Formula $S(O)_pR^3$, wherein p stands for 0, 1 or 2, and $R^3$ denotes straight or branched chained $C_{1-8}$ alkyl, $C_{2-6}$ alkenyl or phenyl-($C_{1-4}$ alkyl), which latter may optionally carry one or more halogen or nitro substituent(s), or phenyl optionally substituted by one or more nitro or trifluoromethyl;

or a group of the Formula $NR^4R^5$, wherein $R^4$ and $R^5$ each represent hydrogen, straight or branched $C_{1-12}$ alkyl, $C_{2-6}$ alkenyl, phenyl-($C_{1-4}$ alkyl) or di-($C_{1-4}$ alkyl)-amino-($C_{1-6}$ alkyl);

$R^1$ and $R^2$ each represent hydrogen or straight or branched chained $C_{1-4}$ alkyl, or $R^1$ and $R^2$ together form a group of the Formula $(CH_2)_n$—Y—$(CH_2)m$, wherein Y stands for a $CH_2$ group, a sulfur atom or a group of the Formula $NR^6$, wherein $R^6$ denotes phenyl-($C_{1-4}$ alkyl), n and m each represent 0, 1, 2, 3, 4 or 5;

Z stands for a group of the Formula $NR^7R^8$, wherein $R^7$ and $R^8$ each represent hydrogen, $C_{2-6}$ alkenyl, $C_{3-8}$ cycloalkyl, adamantyl or phenyl-($C_{1-4}$ alkyl), which latter may optionally carry one or more substituent(s) selected from the group consisting of halogen, hydroxy, $C_{1-4}$ alkyl, $C_{1-4}$ alkoxy, amino and nitro; ($C_{1-4}$ alkyl)-amino-($C_{1-6}$ alkyl), di-($C_{1-4}$ alkyl)-amino-($C_{1-6}$ alkyl) or $C_{1-6}$ alkyl, which latter may optionally be substituted by a hydroxy, amino, carboxy, morpholinocarbonyl, [4-(2-hydroxyethyl)-piperazin-1-yl]-carbonyl, ($C_{1-4}$ alkoxy)-carbonyl or a 5- or 6-membered saturated or unsaturated heterocyclic group containing one or more nitrogen and/or oxygen atom(s) and being optionally condensed with a benzene ring; or $R^7$ and $R^8$ together form a group of the Formula $(CH_2)j$—W—$(CH_2)_k$, wherein j and k each represent 1, 2 or 3, and W stands for oxygen or a $CH_2$ or CHOH group or a group of the Formula $NR^{10}$ wherein $R^{10}$ denotes hydrogen, $C_{1-4}$ alkoxycarbonyl or $C_{1-4}$ alkyl, which latter may optionally carry a substituent selected from the group consisting of hydroxy or phenyl;

or a group of the Formula $SR^9$ wherein $R^9$ stands for $C_{1-4}$ alkyl substituted by a ($C_{1-4}$ alkoxy)-carbonyl group, with the proviso that if Q represents a group of the Formula $S(O)_pR^3$, $R^1$ and $R^2$ are other than hydrogen or $C_{1-4}$ alkyl and with the further proviso that if Q represents morpholino, Z is amino and $R^1$ stands for hydrogen, $R^2$ is other than hydrogen.

The invention encompasses all the tautomeric forms of the compounds of the general Formula (I).

The compounds according to the present invention possess valuable biological properties. They exert primarily positive inotropic and antianginal effects which are complemented by acute antiinflammatory, ulcus and gastric acid secretion inhibiting, furthermore by weaker tranquillant, spasmolytic and analgesic properties.

The term "alkyl group" used throughout the specification relates to straight or branched chained saturated aliphatic hydrocarbon groups containing the given number of carbon atom(s) (e.g. methyl, ethyl, tert-butyl, n-butyl etc.). The term "alkenyl group" designates straight or branched chained aliphatic hydrocarbon groups comprising at least one double bond (e.g. vinyl, allyl, 2-propenyl, methylallyl, butenyl etc.). The term "phenyl-($C_{1-4}$ alkyl)" relates to $C_{1-4}$ alkyl groups in which at least one hydrogen atom is replaced by a phenyl group (e.g. benzyl, 1-phenylethyl, 2-phenylethyl etc.). The "alkylaminoalkyl" and "dialkylaminoalkyl" groups comprise alkyl groups containing the given number of carbon atom(s) (e.g. methylaminomethyl, methylaminoethyl, ethylaminoisopropyl, dimethylaminopropyl, dimethylaminoethyl, diisopropylaminoethyl etc.).

The term "heterocyclic group" relates to 5- or 6-membered aromatic or partially or completely saturated heterocyclic groups comprising one or more nitrogen and/or oxygen atom(s), which may optionally be condensed with a benzene ring (e.g. piperidyl, morpholinyl, piperazinyl, furyl, imidazolyl, pyridyl, pyrimidinyl, pyrazolyl, pyridazinyl, isoxazolyl, pyrrolidinyl, imidazolidinyl, pyrazolinyl, pyranyl, 1-benzyl-piperazin-4-yl, indol-3-yl etc.).

The term "$C_{1-4}$ alkoxycarbonyl group" may be e.g. methoxycarbonyl, ethoxycarboyl, butoxycarbonyl etc. The term "$C_{3-8}$ cycloalkyl group" may be e.g. cyclopropyl, cyclobutyl, cyclopentyl, cyclohexyl etc. The term "halogen atom" encompasses fluorine, chlorine, bromine and iodine.

The pharmaceutically acceptable salts of the compounds of the general Formula (I) can be formed with inorganic or organic acids. As examples for the pharmaceutically acceptable acid-addition salts the hydrochlorides, hydrobromides, sulfates, citrates, maleates, fumarates and ethanesulfonates can be mentioned.

Preferred representatives of the compounds of the general Formula (I) are the following derivatives: 2-(methylthio)-5-{N-(3-morpholinopropyl)}-amino-6,7,8,9-tetrahydro-1,2,4-triazolo[5,1-b]quinazoline, 5-(diethylamino)-7-methyl-2-morpholino-1,2,4-triazolo[1,5-a]pyrimidine, 2-(1-methylethylthio)-5-{N-(3-morpholinopropyl)}-amino- 6,7, 8,9-tetrahydro-1,2,4-triazolo[5,1-b]quinazoline, 2-(ethylthio)-5-{N-(2-morpholinoethyl)}-amino-6,7,8,9-tetrahydro- 1,2,4-triazolo[5,1-b]quinazoline, 2-(methylthio)-5-

[N-(2-morpholinoethyl)]amino-6,7,8,9,10,11,12,13,14,15-decahydro-cyclododeca[d]-1,2,4-triazolo[1,5-a]pyrimidine and pharmaceutically acceptable salts thereof.

According to a further aspect of the present invention there is provided a process for the preparation of -1,2,4-triazolo[1,5-a]pyrimidine derivatives of the general Formula (I) and pharmaceutically acceptable acid addition salts thereof, which comprises reacting a triazolo derivative of the general Formula (II),

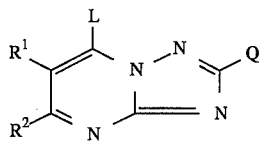

(II)

wherein Q, $R^1$ and $R^2$ are as stated above, L represents a leaving group, preferably halogen, O-trialkylsilyl, O-alkylsulfonyl or O-arylsulfonyl, with an amine or thiol of the general Formula (III),

H—Z       (III)

wherein Z is as stated above, and, if desired, converting a compound of the general Formula (I) into a pharmaceutically acceptable acid-addition salt thereof, or setting free a base of the general Formula (I) from an acid-addition salt thereof, or converting an acid-addition salt of a base of the general Formula (I) into another acid-addition salt.

If the reaction is carried out with an amine, that is with a compound of the general Formula (III), wherein Z is a group of the Formula $NR^7R^8$, an excess thereof may serve as a solvent. In this case at least 2 moles of amine related to 1 mole of the triazolo derivative of the general Formula (II) is used. When using the amine in an equimolar amount, or when reacting a thiol of the general Formula (III), the reaction is performed in a solvent. The compounds of the general Formula (II), wherein L represents halogen, O-alkylsulfonyl or O-arylsulfonyl, are reacted with the compounds of the general Formula (III) in a protic, polar aprotic or apolar aprotic solvent, in the presence of an acid-binding agent. As protic solvent preferably aliphatic alcohols or diols, as polar aprotic solvent preferably acetonitrile, dimethylformamide or tetrahydrofuran, as apolar aprotic solvent preferably benzene or a homologue thereof, 1,2-dichloroethane, chlorobenzene or chloroform are used. As basic acid-binding agent preferably a tertiary base, e.g. triethylamine may be applied.

When reacting compounds of the general Formula (II), wherein L stands for O-trialkylsilyl, with an equimolar amount of amine or with a thiol of the general Formula (III), wherein Z denotes a group of the Formula $SR^9$, the reaction is preferably performed in a polar aprotic or apolar aprotic solvent. As polar aprotic solvent preferably acetonitrile, dimethylformamide or tetrahydrofuran, as apolar aprotic solvent preferably benzene or a homologue thereof, 1,2-dichloroethane or chloroform can be used. One may also proceed by reacting an O-trialkylsilyl ester of the general Formula (II) in situ, that is in the reaction mixture where it was formed, with an amine or thiol of the general Formula (III). In this case an excess of the silylating agent used for the preparation of the compounds of the general Formula (II) may serve as solvent.

The reaction can be performed at any temperature between room temperature and the boiling point of the solvent or amine used in an excess. Preferably it is carried out between 30° C. and 80° C.

The compounds of the general Formula (I) thus obtained can be separated from the reaction mixture by known methods. They crystallize from the reaction mixture either directly or upon adding some water and can be filtered off. If they separate in an oily form, they can be extracted with a water-immiscible organic solvent, evaporated and clarified by methods known per se.

According to our experiments the compounds of the general Formula (II) used as starting substances can be prepared from the known compounds of the general Formula (IV)

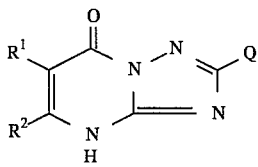

(IV)

by converting the oxo group of a compound of the general Formula (IV) into a leaving group preferably with a mineral halide, silylating agent, alkyl or arylsulfonyl halide.

The amines and thiols of the general Formula (III) are commercial products.

The compounds of the general Formula (I) possess valuable positive inotropic and antianginal effects. These activities are supplemented by acute antiinflammatory, ulcus and gastric acid secretion inhibiting, furthermore by weaker tranquillant, spasmolytic and analgesic properties.

The activity of the compounds of the general Formula (I) is shown by the following tests.

1. Positive inotropic effect in anaesthetized cat

The experiments were carried out on male and female cats anaesthetized with chloralose-urethane (40/300 mg/kg i.p. in a volume of 1 ml/kg). A polyethylene catheter was inserted into the left ventricle via the right subclavian artery. The inotropic activity was measured with the aid of the first derivative by time of the left ventricular pressure curve ($dP/dt_{max}$). The blood pressure was measured by means of another catheter introduced from the left femoral artery into the upper third part of the abdominal artery. A Statham P23Db transducer and HSE (Hugo Sachs Electronics) amplifiers were used for both pressure measurements. The signals thus obtained were recorded by a Lineacorder Mark VII polygraph of WR 3101 type. The test compounds were administered via a femoral venous cannula.

The effects of the compounds are characterized by the positive inotropic responses ($dP/dt_{max}$) shown in Table I.

TABLE I

| | Positive inotropic effect | |
|---|---|---|
| Compound No. of Example | Dose mg/kg i.v. | $dP/dt_{max}$ % |
| 30 | 1 | 22.3 |
| | 5 | 53.8 |
| | 10 | 86.8 |
| 8 | 1 | 42.8 |
| | 5 | 76.0 |
| | 10 | 86.3 |
| 19 | 1 | 35.0 |
| | 5 | 72.8 |
| | 10 | 90.6 |
| 31 | 1 | 46.5 |
| | 5 | 130.8 |
| | 10 | 129.0 |
| 23 | 1 | 36.2 |
| | 5 | 97.6 |

TABLE I-continued

| | Positive inotropic effect | |
|---|---|---|
| Compound No. of Example | Dose mg/kg i.v. | dP/dt$_{max}$ % |
| | 10 | 130.2 |
| 53 | 0.5 | 35.5 |
| | 1.0 | 48.0 |
| | 5.0 | 95.0 |
| | 10.0 | 93.6 |
| Amrinone | 1.0 | 19.0 |
| | 5.0 | 53.9 |
| | 10.0 | 48.3 |
| Trapidil | 1.0 | 56.4 |
| | 5.0 | 67.9 |
| | 10.0 | 42.3 |

From Table I it can be established that the compounds of the general Formula (I) increase the dP/dt$_{max}$ values in a dose-dependent way, the said values being characteristic of the myocardial force. At the same time, in case of both reference compounds the effect does not exceed 50 % even in the highest dose (10 mg/kg). Considering equal doses the compounds according to the invention are 1.5–3.5 times more effective than the reference compounds.

2. Positive inotropic effect in guinea pig

The experiments were carried out by the method of Alousi [Alousi, A. A. et al.: J. Cardiovasc. Pharmacol. 5, 804–811 (1983)]. Animals weighing 400–600 g were stunned with a blow to the head and exsanguinated. The heart was excised and the right atrium was removed and placed into a modified Tyrode solution of 37° C. It was then preloaded with 2.1 g and stimulated electrically at a rate of 2 Hz by rectangular pulses 0.5 ms in duration. The first derivative by time of the contraction force of the isolated organ (dP/dt) and the atrial frequency were recorded by a polygraph. From the data thus obtained percentage changes were calculated. The results are shown in Table II.

TABLE II

| Positive inotropic effect in guinea pig | | |
|---|---|---|
| Compound No. of Example | Concentration force dP/dt (%/) | Frequency (%) |
| 23 | 92 | −21 |
| 8 | 86 | −5 |
| 19 | 171 | −2 |
| 39 | 51 | −12 |
| 46 | 80 | −15 |
| 35 | 79 | 8 |
| Trapidil | 50 | −7 |
| Amrinone | 33 | 28 |

The positive inotropic effect of the compounds considerably surpasses that of the reference substances. Besides, the compounds according to the invention are less tachycardic.

3.a) Antianginal effect in rats

The experiments were carried out by the method of Leitold [Leitold, M. and Laufen, H.: Arzneimittel Forschung 33, 1117–1121 (1983)]. Rats weighing 180–220 g were narcotized with chloralose-urethane (70/700 mg/kg i.p.). The ECG was registered with needle electrodes in standard II leading. The experimental coronaria insufficiency was induced with vasopressin (1 NE/kg i.v.). The height of T wave in ECG was measured before and after the administration of vasopressin in both the control and treated groups. Test compounds were administered intravenously 2 minutes prior to the treatment with vasopressin. The ED$_{50}$ values of the compounds are shown in Table IIIA.

TABLE IIIA

| Antianginal effect | |
|---|---|
| Compound No. of Example | ED$_{50}$ mg/kg i.v. |
| 16 | 1.52 |
| 22 | about 2.00 |
| 9 | about 2.00 |
| 60 | about 2.00 |
| 4 | 1.97 |
| 6 | 1.49 |
| 10 | 1.47 |
| Prenylamine | 6.60 |
| Trapidil results in an inhibition of 38% in a dose of 2 mg/kg | |

From Table IIIA it can be seen that the test compounds are superior to the reference compounds, they are 3–4 times more effective then Prenylamine.

3.b) Coronary flow test in dog

The experiments were carried out in young mongrel do, of both sexes weighing 10–26 kg. The test compounds were administered in 1–5–10 mg/kg doses intravenously. The animals were anaesthetized by pentobarbital (Nembutal, Serva) and artificially ventilated (type: RO-5) In open chest dogs blood flow in the left anterior descending coronary artery was measured continuously by an electromagnetic flowmeter (Godard-Statham, type: SP 2202). Mean arterial blood pressure was recorded on the carotis with a Statham gauge (type: p23Db). The changes of the myocardial contractile forces were followed isometrically with a microdynamometer (type: Experimetria, SG-01) affixed to the anterior wall of the left ventricle. Data were collected on the first derivate of the myocardial contractile force to follow the changes of the contraction and relaxation speed. The data were recorded by an apparatus of Medicor CH-61 type The changes of the tissular flow in the left anterior coronary wall were recorded by the so-called thermoclearance method (Golenhofen 1964) with a Radelkis direct recording apparatus. The changes of the heart rate were also followed. The conductivity of the coronary artery (the ratio of the mean coronary flow and the mean blood pressure) was calculated. The mean values were evaluated statistically using Student's test as well as regression analysis and multiple t test. The data are shown in Table IIIB.

TABLE IIIB

| Coronary flow test in dog | | | |
|---|---|---|---|
| Compound | Conductivity of the coronary artery in % | | |
| No. of Example | Doses: 1 mg/kg | 5 mg/kg | 10 mg/kg |
| 30 | 166 | 397 | 481 |
| 35 | 256 | 940 | 1030 |
| 37 | 188 | 371 | 780 |
| Trapidil* | 165 | 300 | 427 |

*N,N-diethyl-5-methyl-[1,2,4]triazolo[1,5-a-]pyrimidin-7-amine

From the above data it can be seen that the test compounds improve the coronary flow and they are more effective than the reference substance.

4. Antiinflammatory (Carrageen oedema inhibiting) effect

The experiments were carried out by the method of Winter et al. [Winter, C. A. et al.: Proc. Soc. Exp. Biol. Med. 111, 544–547 (1962)] in rats weighing 150 to 180 g. 0.1 ml of a 1 per cent carrageen suspension was injected subcutaneously into the plantar region of one of the hind paws. Rats were fasted for 12 hours and received drinking water ad libitum. One hour before treatment with the test compound the animals were hydrated orally with 30 ml/kg of tap water. The test compounds or the vehicle were administered p.o. in a volume of 10 ml/kg, then one hour later carrageen was applied. The volume of the treated paw was measured by a plethysmometer before and 3 hours after injection in such a way that displacement of the liquid arising from the volume alteration was indicated on a millimeter scale. The volume of the treated paws were compared with those of the control group. The dose resulting in an inhibition of 30 % ($ID_{30}$) was determined by the aid of a line of regression. The results are given in Table IV.

TABLE IV

Antiinflammatory effect

| Compound No. of Example | $ID_{30}$ mg/kg |
|---|---|
| 3 | from 12.5 to 25 |
| 54 | 85.0 |
| 10 | 120.0 |
| 23 | 140.0 |
| 26 | 170.0 |
| 50 | 190.0 |
| 7 | 200.0 |
| Acetylsalicylic acid | 62.4 |
| Paracetamol | 195.3 |

From Table IV it can be seen that one of the test compounds is 3 to 9 times more effective than the reference substances, 3 further derivatives are 1.5 to 2.5 times more effective than Paracetamol and 3 compounds can be considered as effective as Paracetamol.

5. Motility inhibiting activity

The tests were performed according to the method of Borsy et al. [Arch. Int. Pharmacodyn. 124, 1–2 (1960)]. Groups consisting of 3 mice each were treated orally with different doses of the compounds to be tested. Then the test animals were placed in a Dews equipment. In this equipment the number of interruptions of infrared beam within 30 minutes was counted. The inhibition is expressed as the percentage of the value obtained for the control animals. The reference compound (Meprobamate) is inactive in a dose of 100 mg/kg.

TABLE V

| Compound No. of Example | Motiliy inhibition Dose: 100 mg/kg |
|---|---|
| 16 | −53% |
| 25 | −62% |
| 23 | −52% |
| 15 | −65% |
| Meprobamate | $ED_{50}$ = 232 mg/kg |

From Table V it can be established that the activity of the test-compounds surpasses that of the reference substance.

6. Narcosis potentiating activity

Groups consisting of 6 mice each were orally treated with the compound to be examined. After one hour, hexobarbital [5-(1-cyclohexenyl)-1,5-dimethylbarbituric acid] was injected intravenously at a dosage of 40 mg/kg. The control group was treated only with hexobarbital to provoke sleep. The duration of sleep was recorded. If the duration of sleep of an animal exceeded that of the mean value of the control group by a factor of 2.5, it was considered as a positive reaction. The frequency of the positive reaction is expressed as the percentage of the value obtained for the control animals. The reference compound (meprobamate) is inactive in a dose of 100 mg/kg.

TABLE VI

| Compound No. of Example | Narcosis potentiating effect Dose: 100 mg/kg |
|---|---|
| 11 | 67% |
| 25 | 67% |
| 24 | 67% |
| Meprobamate | $ED_{50}$ = 260 mg/kg |

From the above data it can be established that the activity of the test compounds surpasses that of the reference substance.

7. Spasmolytic activity on mice

The tests were carried out according to the modified method of Benzinger and Hane [Arch. Int. Pharmacodyn. 167, 245–249 (1959)]. Mice of both sexes (NMRI breed, body weight 20–25 g) were treated orally with the compounds to be tested. One hour after the administration pentetrazole (6,7,8,9-tetrahydro- 5H-tetrazoloazepine) was given intraperitoneally in a dosis of 125 mg/kg. The tonic-extensoric spasms on the hind limbs were registered. As reference compound 3,5,5-trimethyl-oxazolidine- 2,4-dione (trimetadione) was used. The results are set forth in Table VII.

TABLE VII

| Compound No. of Example | Inhibition of pentetrazole spasm Dose: 100 mg/kg |
|---|---|
| 15 | −50% |
| 18 | −56% |
| Trimetadione | $ED_{50}$ = 400 mg/kg |

From the data of Table VII it can be established that the activity of the test compounds surpasses that of the reference compound.

8. Gastric acid secretion test

The tests were carried out according to the method of Shay [Shay, H. et al.: Gastroenterology 5, 45 (1945)]. Rats of both sexes (Wistar breed, weighing 180–240 g) were fastened for 48 hours. On the day of the test the pylorus of the animals was bound under ether narcosis. The test compounds were administered orally 3 hours before the operation. 4 hours after the operation the animals were anaesthetized and the stomach was removed, the content thereof was centrifuged and the amount of the free acid was determined by titration, in the presence of Töpfer reagent. The inhibition in relation to the control is calculated in percentage. The results are shown in Table VIII.

TABLE VIII

| Compound No. of Example | Dose mg/kg p.o. | Inhibition % |
|---|---|---|
| 23 | 200 | 95 |
| 1 | 200 | 75 |
| Cimetidine | 200 | 91 |
| Trithiozine | 400 | 63 |

From the data of Table VIII it can be established that the test compounds are more effective than the reference compounds.

According to a further aspect of the present invention there are provided pharmaceutical compositions comprising as active ingredient at least one compound of the general Formula (I) or a pharmaceutically acceptable acid-addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potato starch, talc, magnesium carbonate, magnesium stearate, calcium carbonate, stearic acid or the salt thereof can be used. As carrier for the soft gelatine capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in the pharmaceutical industry, e.g. wetting, sweetening agents, aroma substances, salts causing the change of osmotic pressure, buffers, etc. The pharmaceutical formulations may further comprise other active ingredients, too.

The compounds of the general formula (I) can preferably be used in therapy orally in the form of tablets or capsules. Especially preferred are the capsules or talets comprising about 50 mg of active ingredient.

The daily dose of the compounds of the general formula (I) can vary within wide ranges depending on several factors, e.g. on the activity of the active ingredients, the patient's condition and age, the severity of the disease, etc. The oral dose is generally 1 to 1000 mg/day, preferably 10 to 200 mg/day. It has to be stressed that these dose values are only of informative character and the administered dose must always be determined by the physician therapeutist.

According to a further aspect of the present invention there is provided the use of the compounds of the general formula (I) or pharmaceutically acceptable salts thereof for the preparation of pharmaceutical compositions having particularly positive inotropic and antianginal effects.

According to a still further aspect of the present invention there is provided a method of cardiotonic and antianginal treatment which comprises administering to the patient an effective amount of a compound of the general formula (I) or a pharmaceutically acceptable salt thereof.

The invention is further illustrated by the following Examples of non-limiting character.

EXAMPLE 1

5-(Diethylamino)-2-(methylthio)-6,7-dihydro-8H-cyclopenta[ d]-1,2,4-triazolo[1,5-a]pyrimidine 4.81 g (0.02 mole) of 5-chloro-2-(methylthio)-6,7-dihydro- 8H-cyclopenta[d]-1,2,4-triazolo[1,5-a]pyrimidine are suspended in 30 ml of 2-propanol, 2.93 g (0.04 mole) of diethylamine are added to the suspension and the reaction mixture is boiled for 1.5 hours. The solution thus obtained is evaporated to dryness, the crystalline residue is suspended in 40 ml of water, filtered, washed with water, dried and recrystallized from an aqueous methanol solution.

Yield: 5.32 g (96 %) M.p.: 119°–120.5° C.

According to the method of Example 1 the following derivatives are prepared by reacting an appropriate triazolo derivative of the general Formula (II) with an appropriate amine of the general Formula (III):

EXAMPLE 2

5-[N-(3-Hydroxypropyl)]amino-2-(methylthio) -6,7-di hydro-8H-cyclopenta[d]-1,2,4-triazolo[1,5-a]pyrimidine Yield: 5.25 g (94 %) M.p.: 170°–171.5° C. (recrystallized from acetonitrile)

EXAMPLE 3

5-(Allylamino)-2-(methylthio)-6,7-dihydro-8H-cyclopenta[d]-1,2,4-triazolo[1,5-a]pyrimidine Yield: 5.07 g (97 %) M.p.: 166°–167.5° C. (recrystallized from acetonitrile)

EXAMPLE 4

5-(Diallylamino)-2-(methylthio)-6,7-dihydro-8H-cyclopenta[d]-1,2,4-triazolo [1,5-a]pyrimidine Yield: 5.55 g (92 %) M.p.: 110°–111.5° C. (recrystallized from acetonitrile)

EXAMPLE 5

5-(Cyclohexylamino)-2-(methylthio)-6,7-dihydro-8H-cyclopenta[d]-1,2,4-triazolo[1,5-a]pyrimidine Yield: 5.97 g (98%) M.p.: 114°–116° C. (recrystallized from acetonitrile)

EXAMPLE 6

5-(Benzylamino)-2-(methylthio)-6,7-dihydro-8H-cyclopenta[ d]-1,2,4-triazolo[1,5-a]pyrimidine Yield: 5.95 g (95.5%)

M.p: 158°–159.5° C. (recrystallized from acetonitrile)

EXAMPLE 7

5-(4-Chlorobenzylamino)-2-(methylthio)-6,7-dihydro-8H-cyclopenta[ d]-1,2,4-triazolo[1,5-a]pyrimidine Yield: 6.71 g (97%)

M.p: 162°–164° C. (recrystallized from acetonitrile)

EXAMPLE 8

2-(Methylthio)-5-morpholino-6,7-dihydro-8H-cyclopenta[ d]-1,2,4-triazolo[1,5-a]pyrimidine Yield: 5.71 g (98%) M.p.: 162°–163.5° C. (recrystallized from an aqueous methanol solution)

EXAMPLE 9

5-[4-(2-Hydroxyethyl)piperazino]-2-(methylthio)-6,7-dihydro- 8H-cyclopenta[d]-1,2,4-triazolo[1,5-a]pyrimidine Yield: 4.48 g (67%) M.p. 142°–144° C. (recrystallized from methanol)

EXAMPLE 10

2-(Methylthio)-5-[N-(2-morpholinoethyl)]amino-6,7-dihydro-
8H-cyclopenta[d]-1,2,4-triazolo[1,5-a]pyrimidine Yield: 6.55 g (98%) M.p.: 210°–212° C. (recrystallized from methanol)

EXAMPLE 11

5-[N-bis(2-Hydroxyethyl)]amino-2-morpholino-6,7-dihydro-
8H-cyclopenta[d]-1,2,4-triazolo[1,5-a]pyrimidine Yield: 5.5 g (80%) M.p.: 167°–169° C. (recrystallized from an aqueous methanol solution)

EXAMPLE 12

5-[N-(2-Hydroxyethyl)]amino-2-morpholino-6,7-dihydro-
8H-cyclopenta[d]-1,2,4-triazolo[1,5-a]pyrimidine Yield: 4.93 g (81%) M.p.: 216°–217.5° C. (recrystallized from methanol)

EXAMPLE 13

5-(Allylamino)-2-morpholino-6,7-dihydro-8H-
cyclopenta[d]-1,2,4-triazolo[1,5-a]pyrimidine Yield: 5.71 g (95%) M.p.: 165.5°–167° C. (recrystallized from acetonitrile)

EXAMPLE 14

5-(Diallylamino)-2-morpholino-6,7-dihydro-8H-
cyclopenta[d]-1,2,4-triazolo[1,5-a]pyrimidine Yield: 6.60 g (97%) M.p.: 117°–120° C. (recrystallized from cyclohexane)

EXAMPLE 15

2,5-Dimorpholino-6,7-dihydro-8H-cyclopenta
[d]-1,2,4-triazolo[1,5-a]pyrimidine

Yield: 6.08 g (92%) M.p.: 211°–213° C. (recrystallized from an aqueous isopropanol solution)

EXAMPLE 16

2-Morpholino-5-piperidino-6,7-dihydro-8H-
cyclopenta[d]-1,2,4-triazolo[1,5-a]pyrimidine Yield: 6.30 g (96%) M.p.: 207°–208.5° C. (recrystallized from an aqueous methanol solution)

EXAMPLE 17

2-Morpholino-5-[N-(3-morpholinopropyl)]amino-6,7
-dihydro-
8H-cyclopenta[d]-1,2,4-triazolo[1,5-a]pyrimidine Yield: 5.58 g (72%) M.p.: 167°–169° C. (recrystallized from methanol)

EXAMPLE 18

2-(Methylthio)-5-[N-(2-morpholinoethyl)]amino-6,7,
8,9-tetrahydro- 1,2,4-triazolo[5,1-b]quinazoline Yield: 5.85 g (85%) M.p.: 162°–163° C. (recrystallized from isopropanol)

EXAMPLE 19

2-(Methylthio)-5-[N-(3-morpholinopropyl)]amino-
6,7,8,9-tetrahydro-1,2,4-triazolo[5,1-b]quinazoline Yield: 6.13 g (84.5%) M.p.: 163°–164° C. (recrystallized from methanol)

EXAMPLE 20

5-(4-Methylpiperazino)-2-(methylthio)-6,7,8,9-tetrahydro-
1,2,4-triazolo[5,1-b]quinazoline Yield: 5.80 g (91%) M.p.: 174°–175° C. (recrystallized from isopropanol)

EXAMPLE 21

5-(Benzylamino)-9-(morpholino)-6,7,8,9-tetrahydro-
1,2,4-triazolo[5,1-b]quinazoline Yield: 5.32 g (73%) M.p.: 191°–193° C. (recrystallized from acetonitrile)

EXAMPLE 22

5-[N-(3-Dimethylaminopropyl)]amino-2-morpholino-
6,7,8,9-tetrahydro-1,2,4-triazolo[5,1-b]quinazoline Yield: 4.39 g (61%) M.p.: 182°–184° C. (recrystallized from an aqueous methanol solution)

EXAMPLE 23

5-(Diethylamino)-7-methyl-2-morpholino-1,2,4-
triazolo[1,5-a]pyrimidine

Yield: 4.50 g (77.5%) M.p.: 127°–129° C. (recrystallized from ethyl acetate)

EXAMPLE 24

5-[N-Benzyl-N-(2-hydroxyethyl)]amino-7-methyl-2-
morpholino- 1,2,4-triazolo[1,5-a]pyrimidine Yield: 5.34 g (72.5%) M.p.: 159°–160.5° C. (recrystallized from methanol)

EXAMPLE 25

2,5-Dimorpholino-7-methyl-1,2,4-triazolo[1,5-
a]pyrimidine monohydrate

Yield: 6.32 g (98%) M.p.: 188°–190° C. (recrystallized from an aqueous isopropanol solution)

EXAMPLE 26

5-(Diethylamino)-2-(dimethylamino)-7,8-dihydro-
9H-thiopyrano[3,2-d]-1,2,4-triazolo[1,
5-a]pyrimidine Yield: 5.43 g (88.5%) M.p.: 124°–126° C. (recrystallized from ethyl acetate)

EXAMPLE 27

5-[N-(2-Hydroxyethyl)]amino-2-(methylthio)-6,7-dihydro-8H-cyclopenta[d]-1,2,4-triazolo[1,5-a]pyrimidine To a suspension of 4.81 g (0.02 mole) of 5-chloro-2-(methylthio)- 6,7-dihydro-8H-cyclopenta[d]-1,2,4-triazolo-[1,5-a]pyrimidine in 20 ml of 2-propanol 2.44 g (0.04 mole) of 2-aminoethanol are added and the reaction mixture is boiled for 1.5 hours. Then it is cooled, the cold suspension is diluted with water, stirred for a short time, finally the separated crystals are filtered and washed with water.

Yield: 5.04 g (95%) M.p.: 191°–192° C. (recrystallized from methanol)

On proceeding according to the method of Example 27 the following derivatives are prepared by reacting an appropriate triazolo derivative of the general Formula (II) with an appropriate amine of the general Formula (III):

EXAMPLE 28

5-(Diethylamino)-2-(methylthio)-6,7,8,9-tetrahydro-1,2,4-triazolo[5,1-b]quinazoline Yield: 5.13 g (88%) M.p.: 121°–122° C. (recrystallized from ethyl acetate)

EXAMPLE 29

2-(1-Methylethylthio)-5-[N-(2-morpholino-ethyl)]amino-6,7,8,9-tetrahydro-1,2,4-triazolo[5,1-b]quinazoline Yield: 7.08 g (94%) M.p.: 190°–191° C. (recrystallized from acetonitrile)

EXAMPLE 30

2-(1-Methylethylthio)-5-[N-(3-morpholinopropyl)]amino-6,7,8,9-tetrahydro-1,2,4-triazolo[5,1-b]quinazoline Yield: 6.68 g (85.5%) M.p.: 140°–141° C. (recrystallized from ethyl acetate)

EXAMPLE 31

2-(Ethylthio)-5-[N-(2-morpholinoethyl)]amino-6,7,8,9-tetrahydro-1,2,4-triazolo[5,1-b]quinazoline Yield: 6.31 g (87%) M.p.: 156°–158° C. (recrystallized from acetonitrile)

EXAMPLE 32

2-(Ethylthio)-5-[N-(3-morpholinopropyl)]amino-6,7,8,9-tetrahydro-1,2,4-triazolo[5, 1-b]quinazoline Yield: 6.78 g (90%) M.p.: 154°–155° C. (recrystallized from ethyl acetate)

EXAMPLE 33

5-(Diethylamino)-7-methyl-2-morpholino-1,2,4-triazolo[1,5-a]pyrimidine

Yield: 4.36 g (75%) M.p.: 127°–128° C. (recrystallized from ethyl acetate)

EXAMPLE 34

2-(Methylthio)-5-[N-(3-morpholinopropyl)]amino-6,7,8,9-tetrahydro-1,2,4-triazolo[5,1-b]quinazoline Yield: 6.24 g (86%) M.p.: 163.5°–165° C. (recrystallized from isopropanol)

EXAMPLE 35

2-(Methylthio)-5-[N-(2-morpholinoethyl)]amino-6,7,8,9,10,11,12,13,14,15-decahydro-cyclododeca[d]-1,2,4-triazolo[1,5-a]pyrimidine To a suspension of 3.39 g (0.01 mole) of 5-chloro-2-(methylthio)- 6,7,8,9,10,11,12,13,14,15-decahydro-cyclododeca[d]-1,2,4-triazolo[1,5-a]pyrimidine in 10.0 ml of 2-propanol 1.11 g (0.011 mole) of triethylamine and 1.43 g (0.011 mole) of 2-aminoethylmorpholine are successively added, and the reaction mixture is boiled for 2 hours. The 2-propanol is then removed in vacuo, the residue is suspended in water, then the crystals are filtered and washed with water.

Yield: 3.80 g (87.5%) M.p.: 134°–136° C. (recrystallized from ethyl acetate)

On proceeding according to the method of Example 35 the following derivatives are prepared by reacting an appropriate triazolo derivative of the general Formula (II) with an appropriate amine of the general Formula (III):

EXAMPLE 36

2-Morpholino-5-[N-(3-morpholinopropyl)]amino-6,7,8,9-tetrahydro-1,2,4-triazolo[5,1-b]quinazoline Yield: 3.81 g (95%) M.p.: 163°–165° C. (recrystallized from acetonitrile)

EXAMPLE 37

2-(Methylthio)-5-[N-(2-morpholinoethyl)]amino-6,7,8,9-tetrahydro-10H-cyclohepta[d]-1,2,4-triazolo[1,5-a]pyrimidine 4.84 g (0.018 mole) of 5-chloro-2-(methylthio)-6,7,8,9-tetrahydro- 10H-cyclohepta[d]-1,2,4-triazolo[1,5-a]pyrimidine are suspended in 15 ml of 2-propanol, 2.02 g (0.02 mole) of triethylamine and 2.60 g (0.02 mole) of 2-aminoethylmorpholine are successively added to the suspension and it is boiled for 1 hour. The cold suspension is diluted with water, the separated crystals are filtered and washed with water.

Yield: 6.28 g (96%) M.p.: 173°–174° C. (recrystallized from acetonitrile)

On proceeding according to the above Example the following derivatives are prepared by reacting an appropriate triazolo derivative of the general Formula (II) with an appropriate amine of the general Formula (III):

EXAMPLE 38

2-(Methylthio)-5-[N-(3-morpholinopropyl)]amino-6,7,8,9-tetrahydro-10H-cyclohepta[d]-1,2,4-triazolo[1,5-a]pyrimidine Yield: 6.47 g (95%) M.p.: 150.5°–151° C. (recrystallized from acetonitrile)

EXAMPLE 39

2-(Methylthio)-5-[N-(2-morpholinoethyl)]amino-7,8-dihydro-
9H-thiopyrano[3,2-d]-1,2,4-triazolo[1,5-a]pyrimidine Yield: 5.48 g (83%) M.p.: 123°–124.5° C. (recrystallized from acetonitrile)

EXAMPLE 40

2-(Methylthio)-5-[N-(2-piperidinoethyl)]amino-
6,7,8,9-tetrahydro-1,2,4-triazolo[5,1-b]quinazoline Yield: 5.68 g (91%) M.p.: 140°–141° C. (recrystallized from isopropanol)

EXAMPLE 41

2-(Methylthio)-5-[N-(2-pyrrolidinoethyl)]amino-
6,7,8,9-tetrahydro-1,2,4-triazolo[5,1-b]quinazoline Yield: 5.51 g (92%) M.p.: 130°–132° C. (recrystallized from ethyl acetate)

EXAMPLE 42

5-(4-Hydroxybutylamino)-2-(methylthio)-6,7-dihydro-
8H-cyclopenta[d]-1,2,4-triazolo[1,5-a]pyrimidine Yield: 3.67 g (69.5%) M.p.: 140°–142° C. (recrystallized from an aqueous acetone solution)

EXAMPLE 43

7-Benzyl-2-(methylthio)-5-[N-(3-morpholinopropyl)]
amino-6,7,8,9-tetrahydropyrido[4,3-d]-1,2,4-triazolo
[1,5-a]pyrimidine To a suspension of 2.42 g (0.007 mole) of 7-benzyl-5-chloro- 2-(methylthio)-6,7,8,9-tetrahydropyrido[4,3-d]-1,2,4-triazolo[1,5-a]pyrimidine in 10 ml of 2-propanol 2.02 g (0.014 mole) of 3-aminopropylmorpholine are added and the reaction mixture is boiled for 1 hour. Then it is cooled, the separated crystals are filtered and washed with 2 propanol and water.

Yield: 3.00 g (94.5%) M.p.: 166°–168° C. (decomp.) (recrystallized from acetonitrile)

According to the method of Example 43 the following derivatives are prepared by reacting an appropriate triazolo derivative of the general Formula (II) with an appropriate amine of the general Formula (III):

EXAMPLE 44

2-(Methylthio)-5-morpholino-6,7,8,9-tetrahydro-
1,2,4-triazolo[ 5,1-b]quinazoline Yield: 2.08 g (97%) M.p.: 185°–186° C. (recrystallized from acetonitrile)

EXAMPLE 45

2-(Methylthio)-5-piperidino-6,7,8,9-tetrahydro-1,2,4-
triazolo[ 5,1-b]quinazoline Yield: 2.08 g (98%) M.p.: 187°–188° C. (recrystallized from acetonitrile)

EXAMPLE 46

8-Benzyl-2-(methylthio)-5-[N-(2-morpholinoethyl)]
amino-6,7,8,9-tetrahydropyrido[3,4-d]-1,2,4-triazolo
[1,5-a]pyrimidine To a suspension of 4.17 g (0,012 mole) of 8-benzyl-5-chloro- 2-(methylthio)-6,7,8,9-tetrahydropyrido[3,4-d]-1,2,4-triazolo[1,5-a]pyrimidine in 12 ml of 2-propanol 1.215 g (0.012 mole) of triethylamine and 1.56 g (0,012 mole) of 2-aminoethylmorpholine are successively added, and the reaction mixture is boiled for 1.5 hours. The separated crystals are filtered and washed with cold 2-propanol and water.

Yield: 4.64 g (88%) M.p.: 185°–188° C. (decomp.) (recrystallized from acetonitrile)

On proceeding according to the method of Example 46 the following derivatives are prepared by reacting an appropriate triazolo derivative of the general Formula (II) with an appropriate amine of the general Formula (III):

EXAMPLE 47

7-Benzyl-2-(methylthio)-5-[N-(2-morpholinoethyl)]
amino-
6,7,8,9-tetrahydropyrido[4,3-d]-1,2,4-triazolo
[1,5-a]pyrimidine Yield: 4.17 g (79%) M.p.: 151°–153° C. (decomp.) (recrystallized from acetonitrile)

EXAMPLE 48

5-(1-Adamantylamino)-2-(methylthio)-6,7-dihydro-8
H-cyclopenta[ d]-1,2,4-triazolo[1,5-a]pyrimidine Yield: 3.41 g (80%) M.p.: 205°–206.5° C. (recrystallized from acetonitrile)

EXAMPLE 49

5-{N-[2-(1H-Indol-3-yl)ethyl]amino}-2-(methylthio)-
6,7-dihydro-8H-cyclopenta[d]-1,2,4-triazolo[1,5-a]
pyrimidine Yield: 4.15 g (95%) M.p.: 245.5°–247.5° C. (recrystallized from dimethylformamide)

EXAMPLE 50

2-(Methylthio)-5-(4-methoxybenzylamino)-6,7-dihydro-
8H-cyclopenta[d]-1,2,4-triazolo[1,5-a]pyrimidine To a suspension of 5.05 g (0.021 mole) of 5-chloro-2-(methylthio)- 6,7-dihydro-8H-cyclopenta[d]-1,2,4-triazolo[1,5-a]pyrimidine in 30 ml of 2-propanol 6.04 g (0.044 mole) of 4-methoxybenzylamine are added, and the reaction mixture is boiled for 1.5 hours. Then the solvent is removed in vacuo, the residue is taken up in chloroform and washed twice with water. The chloroform phase is dried over anhydrous $Na_2SO_4$ and evaporated in vacuo to constant weight. The oily product is suspended in diethyl ether, then the crystalline product thus obtained is filtered off and washed with diethyl ether.

Yield: 6.35 g (88.5%) M.p.: 130.5°–132° C. (recrystallized from acetonitrile)

EXAMPLE 51

7-Benzyl-5-(diethylamino)-2-(methylthio)-6,7,8,9-tetrahydropyrido[ 4,3-d]-1,2,4-triazolo[1,5-a]pyrimidine 0.69 g (0.002 mole) of 7-benzyl-5-chloro-2-(methylthio)-6,7,8,9-tetrahydropyrido[4,3-d]-1,2,4-triazolo[1,5-a]pyrimidine is suspended in 3.0 ml of 2-propanol. 0.44 g (0.006 mole) of diethylamine are added to the suspension and the reaction mixture is boiled for half an hour. The solution thus obtained is evaporated to dryness in vacuo, the residue is dissolved in chloroform and the solution is extracted twice with ether. The chloroform phase is dried over anhydrous $Na_2SO_4$, evaporated to constant weight in vacuo, the oily product is suspended in ethyl acetate, filtered and washed with cold ethyl acetate.

Yield: 0.53 g (69%) M.p.: 111°–113° C. (recrystallized from ethyl acetate)

EXAMPLE 52

2-(Dimethylamino)-5-[N-(2-morpholinoethyl)]amino-7,8-dihydro-9H-thiopyrano[3,2-d]-1,2,4-triazolo[ 1,5-a]pyrimidine To a suspension of 5.40 g (0.02 mole) of 2-(dimethylamino)- 5-chloro-7,8-dihydro-9H-thiopyrano[3,2-d]-1,2,4-triazolo[ 1,5-a]pyrimidine in 20 ml of 2-propanol 2,125 g (0.021 mole) of triethylamine and 2.73 g (0.021 mole) of 2-aminoethylmorpholine are successively added, and the reaction mixture is boiled for one hour. Upon cooling triethylamine hydrochloride gets separated, which is filtered and washed with 2-propanol. The filtrate is evaporated to dryness in vacuo and the residue is dissolved in chloroform. The solution thus obtained is extracted twice with water, dried over anhydrous $Na_2SO_4$ and evaporated in vacuo. The oily product is suspended in ethyl acetate, the crystalline product thus obtained is filtered off and washed with ethyl acetate.

Yield: 5.42 g (74.5%) M.p.: 110°–113° C. (recrystallized from ethyl acetate)

On proceeding according to the method of Example 52 the following derivatives are prepared by reacting an appropriate triazolo derivative of the general Formula (II) with an appropriate amine of the general Formula (III):

EXAMPLE 53

2-(Dimethylamino)-5-[N-(3-morpholinopropyl)]amino7,8-dihydro-9H-thiopyrano[3,2-d]-1,2,4-triazolo[1,5-a]pyrimidine Yield: 5.35 g (71%) M.p.: 86°–89° C. (recrystallized from ethyl acetate)

EXAMPLE 54

5-(4-Benzylpiperazino)-2-(methylthio)-6,7-dihydro-8H-cyclopenta[d]-1,2,4-triazolo[1,5-a]pyrimidine 9.62 g (0.04 mole) of 5-chloro-2-(methylthio)-6,7-dihydro- 8H-cyclopenta[d]-1,2,4-triazolo[1,5-a]pyrimidine are suspended in 160 ml of 2-propanol. Then 14.17 g (0.14 mole) of triethylamine and 11.47 g (0.046 mole) of N-benzylpiperazine dihydrochloride are successively added to the suspension and it is stirred on a water bath of 30° C. for 8 hours. The separated crystals are filtered and washed with 2-propanol and plenty of water.

Yield: 13.65 g (90%) M.p.: 151°–153° C. (recrystallized from acetone)

EXAMPLE 55

5-[N-(3-Hydroxypropyl)]amino-2-morpholino-6,7-dihydro-8H-cyclopenta[d]-1,2,4-triazolo[1,5-a]pyrimidine To a suspension of 5.59 g (0.02 mole) of 5-chloro-2-morpholino- 6,7-dihydro-8H-cyclopenta[d]-1,2,4-triazolo[1,5-a]pyrimidine in 40 ml of isopropanol 3.15 g (0.042 mole) of 3-amino-1-propanol are added, and the mixture is boiled for 1 hour. The solvent is removed in vacuo, the residue is dissolved in chloroform, treated with a slight amount of silica gel, filtered and evaporated to dryness in vacuo.

Yield: 5.69 g (89.5%) M.p.: 185°–187° C. (recrystallized from acetonitrile)

EXAMPLE 56

5-(Tert-butylamino)-2-(methylthio)-6,7-dihydro-8H-cyclopenta[ d]-1,2,4-triazolo[1,5-a]pyrimidine To a suspension of 1.20 g (0.005 mole) of 5-chloro-2-(methylthio)- 6,7-dihydro-8H-cyclopenta[d]-1,2,4-triazolo[1,5-a]pyrimidine in 10 ml of 2-propanol 3.08 g (0.042 mole) of tert-butylamine are added and the mixture is stirred on an oil bath of 50° C. for 10 hours. The solution thus obtained is evaporated in vacuo, the residue is suspended in water, filtered and washed with water.

Yield: 1.20 g (86%) M.p.: 121°–122.5° C. (recrystallized from ethyl acetate)

EXAMPLE 57

5-(Tert-butylamino)-2-(methylthio)-6,7-dihydro-8H-cyclopenta[ d]-1,2,4-triazolo[1,5-a]pyrimidine 6.02 g (0.025 mole) of 5-chloro-2-(methylthio)-6,7-dihydro- 8H-cyclopenta[d]-1,2,4-triazolo[1,5-a]pyrimidine are suspended in 20 ml of methanol. 7.31 g (0.1 mole) of tert-butylamine are added to the suspension and the reaction mixture is stirred at 25° C. for 10 hours. The solution is evaporated to dryness in vacuo and the residue is suspended in water, then the separated crystals are filtered and washed with water.

Yield: 2.76 g (40%) M.p.: 120°–121.5° C. (recrystallized from a mixture of ethyl acetate and cyclohexane)

EXAMPLE 58

Ethyl (2-morpholino-6,7-dihydro-8H-cyclopenta[d]-1,2,4-triazolo[1,5-a]pyrimidin-5-yl)thioacetate To a suspension of 9.80 g (0.035 mole) of 5-chloro-2-morpholino- 6,7-dihydro-8H-cyclopenta[d]-1,2,4-triazolo[1,5-a]pyrimidine in 70 ml of ethanol 3.90 g (0.0385 mole) of triethylamine and 4.21 g (0.035 mole) of ethyl thioglycolate are subsequently added, and the suspension thickening in a short time is stirred at 30° C. for 2.5 hours. The separated crystals are filtered and washed with an aqueous ethanol solution.

Yield: 11.35 g (89%) M.p.: 123.5°–125.5° C. (recrystallized from an aqueous ethanol solution)

EXAMPLE 59

Ethyl[2-methylthio-6,7-dihydro-8H-cyclopenta[d]-1,2,4-triazolo[1,5-a]pyrimidin-5-yl)thioacetate One proceeds according to Example 58 except that the appropriate methylthio derivative is used as starting substance and the reaction mixture is stirred at 50° C. for 1 hour.

Yield: 9.54 g (84%) M.p.: 108°–109° C. (recrystallized from ethanol)

EXAMPLE 60

Ethyl N-[2-methylthio-6,7-dihydro-8H-cyclopenta[d]-1,2,4-triazolo[1, 5-a]pyrimidin-5-yl]glycinate 17.30 g (0.071 mole) of 5-chloro-2-(methylthio)-6,7-dihydro- 8H-cyclopenta[d]-1,2,4-triazolo[1,5-a]pyrimidine and 14.0 g (0.1 mole) of glycine ethyl ester hydrochloride are suspended in 80 ml of ethanol, then 18.20 g (0.18 mole) of triethylamine are dropped to it. The reaction mixture is stirred at a temperature of 30°–35° C. for 6 hours. The thick suspension is diluted with 250 ml of water, then the separated white crystals are filtered and washed with water.

Yield: 21.67 g (98%) M.p.: 128°–129° C. (recrystallized from an aqueous ethanol solution)

EXAMPLE 61

Ethyl N-[2-methylthio-6,7-dihydro-8H-cyclopenta[d]-1,2,4-triazolo[1,5-a]pyrimidin-5-yl]glycinate One proceeds according to Example 60 except that 1.2 mole of glycine ethyl ester hydrochloride are used, calculated on 1 mole of chloro derivative, and the reaction mixture is stirred at 30°–35° C. for 24 hours. The solvent is removed in vacuo, then the residue is suspended in water, filtered and washed with water.

Yield: 10.94 g (89%) M.p.: 128°–129° C. (recrystallized from an aqueous ethanol solution)

EXAMPLE 62

Ethyl N-[2-morpholino-6,7-dihydro-8H-cyclopenta[d]-1,2,4-triazolo[1,5-a]pyrimidin-5-yl]glycinate To a suspension of 9.80 g (0.035 mole) of 5-chloro-2-morpholino- 6,7-dihydro-8H-cyclopenta[d]-1,2,4-triazolo[ 1,5-a]pyrimidine in 50 ml of ethanol 19.54 g (0.14 mole) of glycine ethyl ester hydrochloride are added. Then 17.71 g (0.175 mole) of triethylamine are dropped to it, and the mixture is stirred on a water bath of 40° C. for 20 hours. The solvent is removed in vacuo, the residual crystalline product is suspended in water, filtered and washed with water. The residue is dissolved in a slight amount of chloroform containing 1% of methanol, treated with a slight amount of silica gel, filtered and evaporated to dryness in vacuo. Thus ethyl N-[2-morpholino-6,7-dihydro-8H-cyclopenta[d]-1,2, 4-triazolo[ 1,5-a]pyrimidin-5-yl]glycinate dihydrate is obtained (m.p.: 78°–82° C.), which is dried in vacuo at a temperature of 60° C. to get the corresponding ethyl ester.

Yield: 7.20 g (61.5%) M.p.: 145°–147° C. (recrystallized from an aqueous ethanol solution)

EXAMPLE 63

2-(Methylthio)-5-morpholino-6,7,8,9-tetrahydro-1,2,4-triazolo[ 5,1-b]quinazoline 0.51 g (0.0017 mole) of 5-bromo-2-(methylthio)-6,7,8,9-tetrahydro- 1,2,4-triazolo[5,1-b]quinazoline is suspended in 2 ml of 2-propanol, 0.30 g (0.0034 mole) of morpholine is added and the reaction mixture is boiled for half an hour. Then the suspension is cooled and the separated crystals are washed successively with 2-propanol, water and 2-propanol again.

Yield: 0.49 g (94%) M.p.: 182°–184° C. (recrystallized from acetonitrile)

EXAMPLE 64

2-(Methylthio)-5-[N-(2-morpholinoethyl)]amino-6,7,8,9-tetrahydro- 1,2,4-triazolo[5,1-b]quinazoline 9.45 g (0.04 mole) of 2-(methylthio)-6,7,8,9-tetrahydro-1,2,4-triazolo[5,1-b]quinazolin-5(10H)-one are suspended in 16.14 g (0.1 mole) of hexamethyldisilazane, 13.02 g (0.1 mole) of 2-aminoethylmorpholine and 0.76 g (0,004 mole) of p-toluenesulfonic acid monohydrate are successively added to the suspension and the reaction mixture is stirred for 6 hours on a oil bath of 170°–175° C. while the hexamethyldisiloxane being formed as a side-product is distilled off. The brown solution is cooled to 90° C. the thick suspension is diluted with 2-propanol and allowed to cool to room temperature. The separated crystals are filtered and washed with 2-propanol.

Yield: 12.87 g (92%) M.p.: 164°–165° C. (recrystallized from isopropanol)

EXAMPLE 65

2-[3-(Dimethylamino)propylamino]-5-[N-(2-morpholinoethyl)] amino-6,7,8,9-tetrahydro-1,2,4-triazolo[5,1-b]quinazoline One proceeds according to Example 64 except that the reaction is carried out at a temperature between 150° and 155° C.

Yield: 9.49 g (78.5%) M.p.: 174°–176° C. (recrystallized from acetonitrile)

EXAMPLE 66

2-[3-(Dimethylamino)propylamino]-5-[N-(3-morpholinopropyl)] amino-6,7,8,9-tetrahydro-1,2,4-triazolo[5,1-b] quinazoline One proceeds according to Example 64 except that the reaction is carried out at a temperature between 150° and 155° C.

Yield: 7.70 g (61.5%) M.p.: 159°–161° C. (recrystallized from acetonitrile)

EXAMPLE 67

2-(Methylsulfonyl)-5-[N-(2-morpholinoethyl)]amino-6,7,8,9-tetrahydro-1,2,4-triazolo[5,1-b]quinazoline To a suspension of 5.37 g (0.02 mole) of 2-(methylsulfonyl)- 6,7,8,9-tetrahydro-1,2,4-triazolo[5,1-b]quinazoline-5(10H)-one in 16.14 g (0.1 mole) of hexamethyldisilazane 13.02 g (0.1 mole) of 2-aminoethylmorpholine and 0.38 g (0,002 mole) of p-toluenesulfonic acid monohydrate are added, and the reaction mixture is stirred on an oil bath of 170 to 175° C. for 16 hours. Upon cooling the brown solution separates into two phases. The upper phase is decanted, the lower thick oily phase is taken up in chloroform and extracted with water. The chloroform solution dried over anhydrous $Na_2SO_4$ is treated with silica gel, evaporated to dryness in vacuo and the residual brown oily product is recrystallized from 15 ml of 2-propanol.

Yield: 3.73 g (49%) M.p.: 162°–164° C. (recrystallized from isopropanol)

EXAMPLE 68

2-(Methylsulfonyl)-5-[N-(2-morpholinoethyl)]amino-6,7,8,9-tetrahydro-1,2,4-triazolo[5,1-b]quinazoline 0.57 g (0.002 mole) of 5-chloro-2-(methylsulfonyl)- 6,7,8,9-tetrahydro-1,2,4-triazolo[5,1-b]quinazoline is suspended in 5 ml of 2-propanol. 0.22 g (0.0022 mole) of triethylamine and 0.29 g (0.0022 mole) of 2-aminoethyl-morpholine are successively added to the suspension and it is boiled at 80° C. for half an hour. The solution thus obtained is evaporated to dryness, the residue is suspended in water, filtered and washed with 2-propanol.

Yield: 0.31 g (40.5%) M.p.: 161°–164° C. (recrystallized from isopropanol)

EXAMPLE 69

{2-[2-Methylthio-6,7-dihydro-8H-cyclopenta [d]-1,2,4-triazolo[ 1,5-a]pyrimidin-5-yl]amino}acetic acid morpholide 1.20 g (0.005 mole) of 5-chloro-(methylthio)-6,7-dihydro- 8H-cyclopenta[d]-1,2,4-triazolo[1,5-a]pyrimidine are suspended in 5 ml of 2-propanol, 0.90 g (0.005 mole) of 4-glycyl-morpholine hydrochloride and 1.01 g (0.01 mole) of triethylamine are successively added to the suspension and it is boiled for 2 hours. The separated crystals are filtered and washed with 2-propanol and water.

Yield: 1.45 g (83%) M.p.: 232°–233.5° C. (recrystallized from methanol)

EXAMPLE 70

2-Methylthio-5-morpholino-6,7,8,9-tetrahydro-1,2,4-triazolo[ 5,1-b]quinazoline

To a suspension of 0.51 g (0.002 mole) of 5-chloro-2-(methylthio)- 6,7,8,9-tetrahydro-1,2,4-triazolo[5,1-b] quinazoline in 2 ml of acetonitrile 0.35 g (0.004 mole) of morpholine is added, and the reaction mixture is boiled for 1 hour. Then it is cooled, 2 ml of water are added, the separated crystals are filtered and washed successively with a slight amount of water and acetonitrile.

Yield: 0.50 g (82%) M.p.: 182°–184.5° C.

EXAMPLE 71

1-[2-{2-Methylthio-6,7-dihydro-8H-cyclopenta[d]-1,2,4-triazolo[1,5-a]pyrimidin-5-yl}amino]acetyl-4-(2-hydroxyethyl)piperazine One proceeds according to Example 70 using the appropriate amine of the general Formula (III) except that the crystals are not-washed with water.

Yield: 1.37 g (70%) M.p.: 203°–204.5° C. (recrystallized from ethanol)

EXAMPLE 72

2-Methylthio-5-morpholino-6,7,8,9-tetrahydro-1,2,4-triazolo[ 5,1-b]quinazoline

One proceeds according to Example 70 except that instead of acetonitrile 2 ml of dimethylformamide are used as solvent.

Yield: 0.39 g (64%) M.p.: 181°–184° C.

EXAMPLE 73

2-Methylthio-5-morpholino-6,7,8,9-tetrahydro-1,2,4-1-triazolo[5,1-b]quinazoline

One proceeds according to Example 70 except that instead of acetonitrile 2 ml of tetrahydrofuran are used as solvent and the reaction mixture is boiled for 3 hours instead of for 1 hour.

Yield: 0.42 g (69%) M.p.: 181°–183° C.

EXAMPLE 74

2-Methylthio-5-morpholino-6,7,8,9-tetrahydro-1,2,4-triazolo[ 5,1-b]quinazoline

One proceeds according to Example 70 except that instead of acetonitrile 2 ml of ethylene glycol are used as solvent and the reaction mixture is boiled for 10 minutes instead of for 1 hour.

Yield: 0.58 g (95%) M.p.: 180°–182° C.

EXAMPLE 75

2-Methylthio-5-morpholino-6,7,8,9-tetrahydro-1,2,4-triazolo[ 5,1-b]quinazoline

One proceeds according to Example 70 except that the reaction is carried out in 1 ml (1.00 g≈0.0115 mole) of morpholine, and the reaction mixture is boiled for 2 hours instead of for 1 hour.

Yield: 0.50 g (82%) M.p.: 180°–182.5° C.

EXAMPLE 76

2-Methylthio-5-morpholino-6,7,8,9-tetrahydro-1,2,4-triazolo[ 5,1-b]quinazoline

To a solution of 0.51 g (0.002 mole) of 5-chloro-2-methylthio- 6,7,8,9-triazolo[5,1-b]quinazoline in 2 ml of benzene 0.35 g (0.004 mole) of morpholine is added, and the reaction mixture is boiled for 1.5 hours. Then the solvent is removed in vacuo, the crystalline residue is suspended in water, filtered and washed successively with a slight amount of water and acetonitrile.

Yield: 0.53 g (87%) M.p.: 182°–184° C.

EXAMPLE 77

2-Methylthio-5-morpholino-6,7,8,9-tetrahydro-1,2,4-triazolo[ 5,1-b]quinazoline

One proceeds according to Example 76 except that instead of benzene 2 ml of chloroform are used as solvent and the reaction mixture is boiled for 2.5 hours instead of for 1.5 hours.

Yield: 0.55 g (90%) M.p.: 182°–183.5° C.

EXAMPLE 78

2-Methylthio-5-morpholino-6,7,8,9-tetrahydro-1,2,4-triazolo[ 5,1-b]quinazoline

To a solution of 0.51 g (0.002 mole) of 5-chloro-2-methylthio- 6,7,8,9-tetrahydro-1,2,4-triazolo[5,1-b]quinazoline in 2 ml of xylene 0.35 g (0,004 mole) of morpholine is added, and the reaction mixture is boiled for 1 hour. Then it is cooled and diluted with diethyl ether. The separated crystals are filtered and washed successively with diethyl ether, a slight amount of water and acetonitrile.

Yield: 0.51 g (83.5%) M.p.: 181°–183.5° C.

EXAMPLE 79

2-Methylthio-5-morpholino-6,7,8,9-tetrahydro-1,2,4-triazolo[ 5,1-b]quinazoline

One proceeds according to Example 78 except that instead of xylene 2 ml of chlorobenzene are used as solvent.

Yield: 0.39 g (64%) M.p.: 181°–183° C.

EXAMPLE 80

5-[N-(2-Morpholinoethyl)]amino-2-diallylamino-6,7-dihydro-8H-cyclopenta[d]-1,2,4-triazolo[1,5-a]pyrimidine A mixture of 0.814 g (0.003 mole) of 2-diallylamino-6,7-dihydro-8H-cyclopenta[d]-1,2,4-triazolo[1,5-a]pyrimidin- 5[9H]-one, 3.87 g (0.024 mole≈5.0 ml) of hexamethyldisilazane, 3.12 g (0.024 mole≈3.12 ml) of 2-morpholinoethylamine and 0.19 g (0.001 mole) of p-toluenesulfonic acid monohydrate is stirred at 160° C. for 3 hours. Then it is cooled to 90° C. and 20 ml of methanol are dropped to it. The mixture is boiled for further 1 hour and evaporated to dryness in vacuo. To the residual brown oil (about 4 g) 20 ml of ether are added, then the separated crystals are filtered and washed with water.

Yield: 0.84 g (73%) M.p.: 131.5°–133.5° C. (after recrystallization from a mixture of cyclohexane and ethyl acetate)

EXAMPLE 81

5-[N-(2-Morpholinoethyl)]amino-2-diallylamino-6,7-dihydro-8H-cyclopenta[d]-1,2,4-triazolo[1,5-a]pyrimidine To a solution of 1.60 g (0.00466 mole) of 2-diallylamino-5-trimethylsilyloxy-6,7-dihydro-8H-cyclopenta[d]-1,2,4-triazolo[ 1,5-a]pyrimidine in 1.55 g (0.0096 mole≈2.0 ml) of hexamethyldisilazane 3.0 g (0.023 mole) of 2-morpholinoethylamine and 0.13 g (0.001 mole) of anhydrous ammonium sulfate are added, and the reaction mixture is stirred at 160° C. for 3 hours. Then it is cooled to 90° C. and 10 ml of methanol are cautiously dropped to it. The mixture is evaporated to dryness and the residue is suspended with water, then the separated crystals are filtered and washed with water.

Yield: 1.50 g (83.8%) M.p.: 132°–133.5° C. (recrystallized from a mixture of cyclohexane and ethyl acetate)

EXAMPLE 82

5-[N-(2-Morpholinoethyl)]amino-2-diallylamino-6, 7-dihydro-8H-cyclopenta[d]-1,2,4-triazolo[1,5-a]pyrimidine To a solution of 0.81 g (0.0028 mole) of 2-diallylamino-5-chloro-6,7-dihydro-8H-cyclopenta[d]-1,2,4-triazolo[1,5-a]pyrimidine in 3 ml of acetonitrile 0.81 g (0.0062 mole) of 2-morpholinoethylamine is added, and the reaction mixture is boiled for 1 hour under stirring. Then it is cooled and 3 ml of water are added. The separated crystals are filtered and washed with a slight amount of a 1:1 mixture of acetonitrile and water.

Yield: 0.45 g (42%) M.p.: 131°–133° C.

EXAMPLE 83

2-Methylsulphenyl-5-[N-(2-morpholinoethyl)]amino-6,7,8,9-tetrahydro-1,2,4-triazolo[5,1-b]quinazoline To a solution of 3.65 g (0.0135 mole) of 5-chloro-2-methylsulphenyl- 6,7,8,9-tetrahydro-1,2,4-triazolo[5,1-b] quinazoline in 15 ml of acetonitrile 3.91 g (0.03 mole) of 2-morpholinoethylamine are added, and the reaction mixture is boiled for 1 hour under stirring. The solution is evaporated to dryness in vacuo and the residual oil is dissolved in 25 ml of water. The aqueous solution is extracted with chloroform, the chloroform phase is washed with water, dried over anhydrous sodium sulfate and evaporated to dryness in vacuo. The residual 4.8 g of oily product gets crystalline upon adding 20 ml of ethyl acetate. The crystals are filtered and washed with a slight amount of ethyl acetate.

Yield: 4.23 g (86%) M.p.: 141°–143° C.

EXAMPLE 84

2-Diallylamino-5-[4-ethoxycarbonylpiperazino]-6,7-dihydro-8H-cyclopenta[d]-1,2,4-triazolo[1,5-a]pyrimidine To a solution of 3.45 g (0,012 mole) of 2-diallylamino-5-chloro-6,7-dihydro-8H-cyclopenta[d]-1,2,4-triazolo[1,5-a]pyrimidine in 10 ml of acetonitrile 1.45 g (0.0143 mole≈2.0 ml) of triethylamine and 2.26 g (0.0143 mole≈2.1 ml) of ethoxycarbonylpiperazine are added, and the reaction mixture is stirred at room temperature for 5 hours. Then further 1.08 g (0.0068 mole≈1.0 ml) of ethoxycarbonylpiperazine are added to the mixture, which is stirred for a further hour and allowed to stand overnight. 10 ml of water are dropped to it under stirring, then the separated crystalline product is filtered and washed with water.

Yield: 2.68 g (54.7%) M.p.: 125°–128° C. (after recrystallization from ethyl acetate)

EXAMPLE 85

2-Diallylamino-5-[4-ethoxycarbonylpiperazino]-6,7-dihydro-8H-cyclopenta[d]-1,2,4-triazolo[1,5-a]pyrimidine maleate 2.06 g (0,005 mole) of the compound prepared according to Example 84 and 0.81 g (0,007 mole) of maleic acid are dissolved in 25 ml of ethyl acetate at 30° C. 30 ml of diethyl ether are added to the solution at the same temperature, and the mixture is allowed to crystallize on standing. Then it is cooled to a temperature between 0° C. and 5° C., the separated crystals are filtered and washed with a slight amount of a 1:1 mixture of ether and ethyl acetate.

Yield: 2.40 g (90.9%) M.p.: 87°–92° C.

EXAMPLE 86

5-[N-Ethyl-N-(a-hydroxyethyl)]amino-2-methylthio-6,7,8,9-tetrahydro-1,2,4-triazolo[5,1-b]quinazoline To a solution of 5.1 g (0.02 mole) of 5-chloro-2-methylthio- 6,7,8,9-tetrahydro-1,2,4-triazolo[5,1-b]quinazoline in 20 ml of acetonitrile 2.23 g (0.022 mole≈3.07 ml) of triethylamine and 3.92 g (0.044 mole≈4.3 ml) of 2-ethylaminoethanol are added, and the reaction mixture is boiled for 4 hours under stirring. Then 80 ml of water are added to the solution while it is still warm. After cooling the separated product is filtered and washed with water and a slight amount of ethyl acetate.

Yield: 3.40 g (55.3%) M.p.: 124°–126° C.

EXAMPLE 87

5-[N-(n-Butyl)-N-(2-hydroxyethyl)]amino-2-morpholino-6,7,8,9-tetrahydro-1,2,4-triazolo[5,1-b]quinazoline To a solution of 1.20 g (0.0041 mole) of 5-chloro-2-morpholino- 6,7,8,9-tetrahydro-1,2,4-triazolo[5,1-b]quinazoline in 5 ml of acetonitrile 1.17 g (0.01 mole≈1.31 ml) of 2-(n-butylamino)ethanol are added and the reaction mixture is boiled for 4 hours under stirring. The solution thus obtained is evaporated to dryness in vacuo. The residue is dissolved in a mixture of 20 ml of chloroform and 20 ml of water. The phases are separated, the chloroform phase is dried and evaporated to dryness in vacuo. Thus 1.56 g of yellow oily product is obtained, which is purified by chromatography on a Kieselgel 60H layer (eluent: a mixture of benzene and chloroform) and recrystallized from a mixture of ether and acetone.

Yield: 0.81 g (55.1%) M.p.: 90°–92° C.

EXAMPLE 88

2-Methylthio-5-morpholino-6,7,8,9,10,11-hexahydrocycloocta[d]-1,2,4-triazolo[1,5-a]pyrimidine To a solution of 0.10 g (0.00035 mole) of 5-chloro-2-methylthio- 6,7,8,9,10,11-hexahydrocycloocta[d]-1,2,4-triazolo[ 1,5-a]pyrimidine in 2 ml of acetonitrile 0.13 g (0.0015 mole≈0.13 ml) of morpholine is added, and the reaction mixture is boiled for 2 hours. Upon adding 6 ml of water to the hot solution crystals get separated, which are cooled and washed with water and a slight amount of icy acetonitrile.

Yield: 0.068 g (58.1%) M.p.: 172.5°–173.5° C. (after recrystallization from ethyl acetate)

EXAMPLE 89

2-Methylthio-5-morpholino-6,7,8,9,10,11,12,13,14,15-decahydro-cyclododeca[d]-1,2,4-triazolo[1,5-a]pyrimidine To a solution of 0.13 g (0.00038 mole) of 5-chloro-2-methylthio- 6,7,8,9,10,11,12,13,14,15-decahydro-cyclododeca[d]-1,2,4-triazolo[1,5-a]pyrimidine in 2 ml of acetonitrile 0.13 g (0.0015 mole≈0.13 ml) of morpholine is added, and the reaction mixture is boiled for 2 hours under stirring. Upon dropping 6 ml of water to the solution thus obtained crystals get separated. After cooling the product is filtered and washed with water and a slight amount of icy acetonitrile.

Yield: 0.123 g (83.1%) M.p.: 151°–153° C. (after recrystallization from acetonitrile)

EXAMPLE 90

5-Benzylamino-2-(4-methylpiperazino)-6,7-dihydro-8H-cyclopenta[d]-1,2,4-triazolo[1,5-a]pyrimidine A mixture of 1.34 g (0.0049 mole) of 2-(4-methylpiperazino)- 6,7-dihydro-8H-cyclopenta[d]-1,2,4-triazolo[1,5-a]pyrimidin-5(9H)-one, 8.07 g (0.05 mole≈10.4 ml) of hexamethyldisilazane, 5.36 g (0.05 mole≈5.46 ml) of benzylamine and 0.1 g (0,001 mole) of p-toluenesulfonic acid monohydrate are stirred on an oil bath of 160°–165° C. for 12 hours. After cooling 20 ml of methanol are added to the reaction mixture which is boiled further for 1 hour, then evaporated to dryness in vacuo. 4 ml of ethyl acetate are added to the residual brown oil (about 3 g). The separated crystals are filtered and washed with a slight amount of cold ethyl acetate.

Yield: 1.37 g (77.4%) M.p.: 195°–197° C. (after recrystallization from acetonitrile)

EXAMPLE 91

5-[N-(3,4-Dihydroxyphenylethyl)amino]-2-ethylamino-6,7-dihydro-8H-cyclopenta[d]-1,2,4-triazolo[1,5-a]pyrimidine A mixture of 2.85 g (0.012 mole) of 2-ethylamino-5-chloro- 6,7-dihydro-8H-cyclopenta[d]-1,2,4-triazolo[1,5-a]pyrimidine, 20 ml of isopropanol, 2.53 g (0.025 mole≈3.5 ml) of triethylamine and 2.81 g (0.012 mole) of 2-(3,4-dihydroxyphenyl)ethylamine hydrobromide is stirred on an oil bath of 100° C. for 1 hour. Upon cooling the solution gets crystalline. The separated crystals are filtered and washed successively with water, isopropanol and ether.

Yield: 3.73 g (87.7%) M.p.: 254°–258° C. (decomp.) (after recrystallizaton from acetic acid)

EXAMPLE 92

5-Diisopropylamino-7-methyl-2-morpholino-1,2,4-triazolo[ 1,5-a]pyrimidine

To a solution of 2.54 g (0.01 mole) of 5-chloro-7-methyl-2-morpholino-1,2,4-triazolo[1,5-a]pyrimidine in 10 ml of dimethylformamide 2.02 g (0.02 mole≈2.8 ml) of diisopropylamine are added, and the reaction mixture is boiled for 24 hours under stirring. The solution thus obtained is evaporated to dryness in vacuo and the residue is recrystallized from 20 ml of water.

Yield: 1.5 g (47.1%) M.p.: 134°–136° C.

EXAMPLE 93

2-Morpholino-5-[N-(3-morpholinopropyl)amino]-6,8-dihydro-9H-thiopyrano[4,3-d]-1,2,4-triazolo[1,5-a]pyrimidine To a solution of 2.43 g (0.0078 mole) of 5-chloro-2-morpholino- 6,8-dihydro-9H-thiopyrano[4,3-d]-1,2,4-triazolo [1,5-a]pyrimidine in 15 ml of acetonitrile 1.44 g (0.01 mole≈1.46 ml) of 3-morpholinopropylamine and 1.01 g (0.01 mole≈1.39 ml) of triethylamine are added, and the reaction mixture is boiled for 1 hour under stirring. Then it is cooled and the separated product is filtered and washed with water and acetonitrile.

Yield: 3.02 g (92.3%) M.p.: 173°–176° C. (after recrystallization from acetonitrile)

EXAMPLE 94

2-Ethylamino-5-morpholino-6,7-dihydro-8H-cyclopenta[d]- 1,2,4-triazolo[1,5-a]pyrimidine To a solution of 0.96 g (0,004 mole) of 2-ethylamino-5-chloro- 6,7-dihydro-8H-cyclopenta[d]-1,2,4-triazolo[1,5-a]pyrimidine in 5 ml of acetonitrile 0.87 g (0.01 mole≈0.87 ml) of morpholine is added, and the reaction mixture is boiled for 1.5 hours under stirring. Then it is cooled and 10 ml of water are added. The separated product is filtered and washed with water and icy acetonitrile.

Yield: 1.04 g (90%) M.p.: 278°–283° C. (decomp.)

EXAMPLE 95

2,5-Dimorpholino-6,7,8,9,10,11-hexahydro-cycloocta[d]- 1,2,4-triazolo[1,5-a]pyrimidine A mixture of 0.30 g (0.00093 mole) of 5-chloro-2-morpholino- 6,7,8,9,10,11-hexahydro-cycloocta[d]-1,2,4-triazolo[1,5-a]pyrimidine, 3 ml of acetonitrile and 0.26 g (0.003 mole≈0.26 ml) of morpholine is boiled for 2 hours under stirring. The warm reaction mixture is diluted with 3 ml of water and cooled. The separated crystals are filtered and washed with water and icy acetonitrile.

Yield: 0.28 g (80.0%) M.p.: 227°–229° C. (after recrystallization from acetonitrile)

EXAMPLE 96

2,5-Dimorpholino-6,7,8,9,10,11,12,13,14,15-decahydrocyclododeca[d]-1,2,4-triazolo[1,5-a]pyrimidine To a solution of 0.30 g (0.0008 mole) of 5-chloro-2-morpholino- 6,7,8,9,10,11,12,13,14,15-decahydro-cyclododeca[d]-1,2,4-triazolo[1,5-a]pyrimidine-5[16H]-one in 2.0 ml of acetonitrile 0.26 g (0.003 mole≈0.26 ml) of morpholine is added, and the reaction mixture is boiled for 2 hours. 3 ml of water are added to the warm solution. The crystals separated upon cooling are filtered and washed with water and icy acetonitrile.

Yield: 0.29 g (85.3%) M.p.: 188°–190° C. (after recrystallization from acetonitrile)

EXAMPLE 97

5-(4-Methylpiperazino)-2-morpholino-6,7,8,9-tetrahydro- 1,2,4-triazolo[5,1-b]quinazoline A mixture of 8.81 g (0.03 mole) of 5-chloro-2-morpholino- 6,7,8,9-tetrahydro-1,2,4-triazolo[5,1-b]quinazoline, 6.01 g (0.06 mole) of N-methylpiperazine and 30 ml of isopropanol is boiled for 1 hour under stirring, then it is evaporated to dryness in vacuo. The residue is triturated with 50 ml of water, the crystalline product is filtered and washed with water.

Yield: 9.7 g (90.5%) M.p.: 196°–197° C. (after recrystallization from acetonitrile)

EXAMPLE 98

5-Morpholino-2-(n-octylamino)-6,7-dihydro-8H-cyclopenta[d]-1,2,4-triazolo[1,5-a]pyrimidine To a solution of 1.20 g (0.0037 mole) of 5-chloro-2-(n-octylamino)- 6,7-dihydro-8H-cyclopenta[d]-1,2,4-triazolo[1,5-a]pyrimidine in 5 ml of acetonitrile 0.96 g (0.011 mole) of morpholine are added, and the reaction mixture is boiled for 1.5 hours under stirring. To the warm solution 5 ml of water are added. The crystals separated upon cooling are filtered and washed with water.

Yield: 1.23 g (89.1%) M.p.: 179°–181° C. (after recrystallization from acetonitrile)

EXAMPLE 99

5-[N-(2-Morpholinoethyl)amino]-2-(n-hexylthio)-6,7,8,9-tetrahydro-1,2,4-triazolo[5,1-b]quinazoline To a solution of 6.73 g (0.0207 mole) of 2-(n-hexylthio)-5-chloro-6,7,8,9-tetrahydro-1,2,4-triazolo[5,1-b]quinazoline in 30 ml of acetonitrile 2.23 g (0.022 mole≈3.07 ml) of triethylamine and 2.86 g (0,022 mole≈2.9 ml) of 2-morpholinoethylamine are added, and the reaction mixture is boiled for 1.5 hours under stirring. 30 ml of water are added to the warm mixture. The crystals separated upon cooling are filtered and washed with water.

Yield: 7.78 g (89.8%)

m.p.: 107°–108° C. (after recrystallization from ethyl acetate)

EXAMPLE 100

2-(Allylthio)-5-[N-(2-morpholinoethyl)amino]-6,7,8,9-tetrahydro-1,2,4-triazolo[5,1-b]quinazoline To a solution of 5.0 g (0.0178 mole) of 2-allylthio-5-chloro- 6,7,8,9-tetrahydro-1,2,4-triazolo[5,1-b]quinazoline in 15 ml of acetonitrile 2.02 g (0.02 mole≈2.79 ml) of triethylamine and 2.60 g (0.02 mole≈2.60 ml) of 2-morpholinoethylamine are added. The reaction mixture is boiled for 1 hour under stirring and then 30 ml of water are added. The crystals separated upon cooling are filtered and washed with water.

Yield: 5.80 g (87%) M.p.: 129.5°–130.5° C. (after recrystallization from acetonitrile)

EXAMPLE 101

2-Benzylthio-5-[N-(2-morpholinoethyl)amino]-6,7,8,9-tetrahydro-1,2,4-triazolo[5,1-b]quinazoline To a solution of 2.81 g (0.0085 mole) of 2-benzylthio-5-chloro-6,7,8,9-tetrahydro-1,2,4-triazolo[5,1-b]quinazoline in 10 ml of acetonitrile 1.01 g (0.01 mole≈1.39 ml) of triethylamine and 1.30 g (0.01 mole≈1.30 ml) of 2-morpholinoethylamine are added, and the reaction mixture is boiled for 1.5 hours under stirring. 10 ml of water are added to the warm solution, then the mixture is cooled, and the separated crystals are filtered and washed with water.

Yield: 3.23 g (89.5%) M.p.: 139°–140° C. (after recrystallization from acetonitrile)

EXAMPLE 102

2-Benzylthio-5-[N-(3-morpholinopropyl)amino]-
6,7,8,9-tetrahydro-1,2,4-triazolo[5,1-b]quinazoline To a solution of 2.33 g (0.007 mole) of 2-benzylthio-5-chloro- 6,7,8,9-tetrahydro-1,2,4-triazolo[5,1-b]quinazoline in 8 ml of acetonitrile 0.91 g (0.009 mole≈1.25 ml) of triethylamine and 1.30 g (0.009 mole≈1.32 ml) of 3-morpholinopropylamine are added, and the reaction mixture is boiled for 2 hours under stirring. 8 ml of water are added to the warm solution, then the mixture is cooled, and the acetonitrile is distilled off in vacuo. The residual aqueous solution is extracted with 10 ml of chloroform, the chloroform phase is dried over sodium sulfate and evaporated to dryness in vacuo. The oily product thus obtained gets crystalline upon adding a slight amount of ether. The separated crystals are filtered and washed with ether.

Yield: 2.63 g (86.6%) M.p.: 114.5°–116° C. (after recrystallization from ethyl acetate)

EXAMPLE 103

2-Methylthio-5-piperazino-6,7,8,9-tetrahydro-
1,2,4-triazolo[5,1-b]quinazoline

To a solution of 0.64 g (0.0025 mole) of 5-chloro-2-methylthio- 6,7,8,9-tetrahydro-1,2,4-triazolo[5,1-b]quinazoline in 10 ml of acetonitrile 0.43 g (0.005 mole) of anhydrous piperazine is added, and the reaction mixture is boiled for 1.5 hours under stirring. Then it is cooled, the separated crystals are filtered and washed four times with 5 ml of acetonitrile each. The acetonitrile filtrates are combined and evaporated to dryness in vacuo. The residual crystals are suspended in a slight amount of water, filtered again and washed with water and ether.

Yield: 0.55 g (72.4%) M.p.: 171°–172.5° C. (after recrystallization from ethyl acetate)

EXAMPLE 104

5-[N-(a-Morpholinoethyl)amino]-2-[4-nitrobenzylthio]-
6,7,8,9-tetrahydro-1,2,4-triazolo[5,1-b]quinazoline A mixture of 0.92 g (0.00245 mole) of 5-chloro-2-(4-nitrobenzylthio)- 6,7,8,9-tetrahydro-1,2,4-triazolo[5,1-b]quinazoline, 5 ml of dichloroethane, 0.28 g (0.0027 mole≈0.38 ml) of triethylamine and 0.35 g (0.0027 mole≈0.35 ml) of 2-morpholinoethylamine is boiled for 1 hour under stirring. Then it is cooled, 5 ml of water are added, the phases are separated, the dichloroethane phase is dried over anhydrous sodium sulfate and evaporated to dryness in vacuo.

Yield: 0.98 g (85.2%) M.p.: 165°–167° C. (after recrystallization from acetonitrile)

EXAMPLE 105

2-(4-Chlorobenzylthio)-5-[N-(2-morpholinoethyl)
amino] -6,7,8,9-tetrahydro[5,1-b]quinazoline A mixture of 0.80 g (0.0022 mole) of 5-chloro-2-(4-chlorobenzylthio)- 6,7,8,9-tetrahydro-1,2,4-triazolo[ 5,1-b]quinazoline, 5 ml of dichloroethane, 0.25 g (0.0025 mole≈0.35 ml) of triethylamine and 0.325 g (0.0025 mole≈0.33 ml) of 2-morpholinoethylamine is boiled for 4 hours under stirring. Then it is cooled, 5 ml of dichloroethane and 10 ml of water are added, the phases are separated, the organic phase is extracted with a saturated sodium chloride solution, dried over anhydrous sodium sulfate and evaporated to dryness in vacuo.

Yield: 0.77 g (76.2%) M.p.: 136°–137.5° C. (after recrystallization from acetonitrile)

EXAMPLE 106

5-[N-(2-Morpholinoethyl)amino]-2-(2-nitro-4-
trifluoromethylphenylthio)-
6,7,8,9-tetrahydro-1,2,4-triazolo[5,1-b]quinazoline To a solution of 0.95 g (0.0022 mole) of 5-chloro-2-(2-nitro- 4-trifluoromethylphenylthio)-6,7,8,9-tetrahydro- 1,2, 4-triazolo[5,1-b]quinazoline in 10 ml of acetonitrile 0.24 g (0.0024 mole≈0.33 ml) of triethylamine and 0.31 g (0.0024 mole≈0.31 ml) of 2-morpholinoethylamine are added, and the reaction mixture is boiled for 2 hours under stirring. The solution thus obtained is evaporated to dryness in vacuo, the residue is dissolved in a mixture of 10 ml of water and 15 ml of chloroform, the aqueous phase is extracted with 10 ml of chloroform, the chloroform phases are combined, extracted with water, dried over anhydrous sodium sulfate and evaporated to dryness in vacuo. To the residual oily product a slight amount of diisopropyl ether and a few drops of ethyl acetate are added. The separated crystals are filtered and washed with diisopropyl ether.

Yield: 0.42 g (36.5%) M.p.: 124°–126° C.

EXAMPLE 107

5-Diethylamino-6,7,8,9-tetrahydro-1,2,4-triazolo[ 5,1-b] quinazoline

A mixture of 4.17 g (0.02 mole) of 5-chloro-6,7,8,9-tetrahydro- 1,2,4-triazolo[5,1-b]quinazoline, 20 ml of isopropanol and 4.39 g (0.06 mole) of diethylamine is stirred at 60° C. for half an hour. Then it is cooled, 80 ml of water are added and the mixture is extracted twice with 30 ml of chloroform each. The chloroform phases are combined, extracted with water, dried over anhydrous sodium sulfate and evaporated again to dryness in vacuo.

Yield: 4.75 g (96.7%) M.p.: 104.5°–105° C. (after recrystallization from n-hexane)

EXAMPLE 108

5-[N-(2-Morpholinoethyl)amino]-6,7,8,9-tetrahydro-
1,2,4-triazolo[5,1-b]quinazoline A mixture of 4.17 g (0.02 mole) of 5-chloro-6,7,8,9-tetrahydro- 1,2,4-triazolo[5,1-b]quinazoline, 20 ml of isopropanol, 2.12 g (0.021 mole≈2.93 ml) of triethylamine and 2.73 g (0,021 mole) of 2-morpholinoethylamine is boiled for 1.5 hours under stirring. 60 ml of water are added to the warm solution, and the mixture is cooled, then the separated product is filtered and washed with water.

Yield: 5.60 g (92.6%) M.p.: 200.5°–201.5° C. (after recrystallization from acetonitrile)

EXAMPLE 109

2-Benzylamino-5-[N-(2-morpholinoethyl)amino]-
6,7,8,9-tetrahydro- 1,2,4-triazolo[5,1-b]quinazoline A mixture of 3.14 g (0.01 mole) of 2-benzylamino-5-chloro- 6,7,8,9-tetrahydro-1,2,4-triazolo[5,1-b]quinazoline, 25 ml of isopropanol, 1.11 g (0.011 mole≈1.53 ml) of triethylamine and 1.43 g (0.011 mole≈1.43 ml) of 2-morpholinoethylamine is stirred on an oil bath of 100° C. for half an hour. 25 ml of water are added to the warm reaction mixture, then it is stirred until it gets cool. The separated product is filtered and washed with water and a slight amount of isopropanol.

Yield: 3.88 g (95.2%) M.p.: 192°–194° C. (after recrystallization from methanol)

EXAMPLE 110

2-(Dimethylamino-5-[N-(2-hydroxyethyl)amino]-7,8-dihydro-9H-thiopyrano[3,2-d]-1,2,4-triazolo[1,5-a]pyrimidine A mixture of 1.35 g (0,005 mole) of 2-dimethylamino-5-chloro- 7,8-dihydro-9H-thiopyrano[3,2-d]-1,2,4-triazolo[1,5-a]pyrimidine, 5 ml of isopropanol and 0.61 g (0.01 mole) of ethanolamine is boiled for half an hour under stirring. 10 ml of water are added to the warm solution. The mixture is cooled, then the separated product is filtered and washed with water and cold isopropanol.

Yield: 1.27 g (86.4%) M.p.: 187°–189° C. (after recrystallization from acetonitrile)

EXAMPLE 111

5-Amino-2-methylthio-6,7-dihydro-8H-cyclopenta[d]-1,2,4-triazolo[1,5-a]pyrimidine A mixture of 1.45 g (0,006 mole) of 5-chloro-2-methylthio- 6,7-dihydro-8H-cyclopenta[d]-1,2,4-triazolo[1,5-a]pyrimidine, 10 ml of ethanol and 2.5 ml (0.03 mole) of concentrated ammonium hydroxide is stirred at room temperature for 2 hours. The separated crystalline product is filtered and washed with cold ethanol.

Yield: 0.8 g (60%) M.p.: 305°–307° C. (decomp.)

EXAMPLE 112

2-Methylthio-5-morpholino-6,7,8,9-tetrahydro-1,2,4-triazolo[ 5,1-b]quinazoline

A mixture of 0.098 g (0.00025 mole) of 5-(4-methylphenylsulfonyloxy)- 2-methylthio-6,7,8,9-tetrahydro-1,2,4-triazolo[ 5,1-b]quinazoline, 2 ml of acetonitrile and 0.13 g (0.0015 mole) of morpholine is boiled for 2 hours under stirring. Then it is cooled and evaporated to dryness in vacuo. The residue is dissolved in a mixture of 10 ml of chloroform and 10 ml of water, the phases are separated, the chloroform phase is extracted with 5 ml of 1N sodium hydroxide solution and water, dried and evaporated.

Yield: 0.29 g (38%) M.p.: 183°–185° C. (after recrystallization from acetonitrile)

EXAMPLE 113

2-Methylthio-5-morpholino-6,7,8,9-tetrahydro-1,2,4-triazolo[ 5,1-b]quinazoline

A mixture of 0.03 g (0.0001 mole) of 5-(methanesulfonyloxy)-2-methylthio-6,7,8,9-tetrahydro- 1,2,4-triazolo[5,1-b]quinazoline, 1 ml of acetonitrile and 0.085 g (0.00075 mole) of morpholine is boiled for 1 hour under stirring. Then it is cooled and evaporated to dryness in vacuo. The residue is dissolved in a mixture of 5 ml of chloroform and 5 ml of water, the phases are separated, the chloroform phase is extracted with 1 ml of 1N sodium hydroxide solution and water, dried and evaporated.

Yield: 0.01 g (36%) M.p.: 182°–185° C. (after recrystallization from acetonitrile)

EXAMPLE 114

5-[(4-Hydroxypiperidino)]-2-methylthio-6,7,8,9-tetrahydro-1,2,4-triazolo[5,1-b]quinazoline To a solution of 5.1 g (0.02 mole) of 5-chloro-2-methylthio- 6,7,8,9-tetrahydro-1,2,4-triazolo[5,1-b]quinazoline in 30 ml of acetonitrile 6.47 g (0,064 mole) of 4-hydroxypiperidine are added, and the reaction mixture is stirred at room temperature for 10 hours. Then 30 ml of water are added, the mixture is stirred for a further hour, then the separated product is filtered and washed with water and cold acetonitrile.

Yield: 5.71 g (89.2%) M.p.: 223°–224.5° C. (after recrystallization from acetonitrile)

EXAMPLE 115

2-(3-Dimethylaminopropylamino)-5-morpholino-6,7-dihydro-8H-cyclopenta[d]-1,2,4-triazolo[1,5-a]pyrimidine To a solution of 1.77 g (0.006 mole) of 2-(3-dimethylaminopropylamino)- 5-chloro-6,7-dihydro-8H-cyclopenta[d]-1,2,4-triazolo[1,5-a]pyrimidine in 15 ml of chloroform 1.92 g (0,022 mole≈1.92 ml) of morpholine are added, and the reaction mixture is boiled for 1.5 hours under stirring. Then it is cooled, extracted with 20 ml of water, dried and evaporated to dryness in vacuo.

Yield: 1.3 g (62.8%) M.p.: 210°–213° C. (after recrystallization from acetonitrile)

EXAMPLE 116

5-(2,3-Dichloro-6-aminobenzylamino)-2-morpholino-6,7-dihydro-8H-cyclopenta[d]-1,2,4-triazolo[1,5-a]pyrimidine A mixture of 1.38 g (0.005 mole) of 5-chloro-2-morpholino- 6,7-dihydro-8H-cyclopenta[d]-1,2,4-triazolo[ 1,5-a]pyrimidine, 8 ml of isopropanol, 1.13 g (0.005 mole) of 2,3-dichloro-6-aminobenzylamine hydrochloride and 1.5 ml (0.015 mole) of triethylamine is boiled for 1.5 hours under stirring. Then it is cooled and evaporated to dryness in vacuo. The residue is suspended in 20 ml of water, filtered and washed with water.

Yield 2.14 g (98.5.%) M.p.: 255°–258° C. (recrystallized from dimethylformamide)

EXAMPLE 117

5-(2-Methylbenzylamino)-2-morpholino-6,7-dihydro-8H-cyclopenta[ d]-1,2,4-triazolo[1,5-a]pyrimidine To a solution of 2.78 g (0.01 mole) of 5-chloro-2-morpholino- 6,7-dihydro-8H-cyclopenta[d]-1,2,4-triazolo[ 1,5-a]pyrimidine in 15 ml of chloroform 1.34 g (0.011 mole) of 2-methylbenzylamine and 1.0 g (0.01 mole≈1.5 ml) of triethylamine are added, and the reaction mixture is boiled for 4 hours. Then it is cooled, and the separated product is filtered and washed with water and cold isopropanol.

Yield: 2.93 g (80.5%) M.p.: 97°–99° C.

EXAMPLE 118

5-Morpholino-2-(4-methylpiperazino)-6,7-dihydro-8H-cyclopenta[d]-1,2,4-triazolo[1,5-a]pyrimidine To a solution of 2.93 g (0.01 mole) of 5-chloro-2-(4-methylpiperazino)- 6,7-dihydro-8H-cyclopenta[d]-1,2,4-triazolo[1,5-a]pyrimidine in 15 ml of chloroform 1.92 g (0.022 mole≈1.92 ml) of morpholine are added, and the reaction mixture is boiled for 4 hours. Then it is cooled and evaporated to dryness in vacuo. The residue is suspended in 50 ml of water, filtered and washed with water and isopropanol.

Yield: 2.16 g (63.0%) M.p.: 165°–167° C.

EXAMPLE 119

5-Morpholino-2-piperidino-6,7-dihydro-8H-cyclopenta[d]-1,2,4-triazolo[1,5-a]pyrimidine To a solution of 2.78 g (0.01 mole) of 5-chloro-2-piperidino-6,7-dihydro-8H-cyclopenta[d]- 1,2,4-triazolo[1,5-a]pyrimidine in 15 ml of chloroform 1.92 g (0,022 mole 1.92 ml) of morpholine are added, and the reaction mixture is boiled for 2 hours under stirring. Then it is cooled and evaporated to dryness in vacuo. The residue is suspended in ml of water, filtered and washed with water and a slight amount of isopropanol.

Yield: 3.24 g (98.8%) M.p.: 187°–189° C.

EXAMPLE 120

3-[N-Methyl-N-(2-morpholino-6,7-dihydro-8H-cyclopenta[d]-1,2,4-triazolo[1,5-a]pyrimidin-5-yl)-aminopropylamine and N-{3-[N'-(2-morpholino-6,7-dihydro-8H-cyclopenta[d]-1,2,4-triazolo[1,5-a]pyrimidin-5-yl)]aminopropyl}-N-methyl-amine A mixture of 5.54 g (0.02 mole) of 5-chloro-2-morpholino-6,7-dihydro-8H-cyclopenta[d]-1,2,4-triazolo[1,5-a]pyrimidine, 30 ml of isopropanol and 3.52 g (0.04 mole≈2.95 ml) of 3-methylaminopropylamine is boiled for 1.5 hours under stirring. Then it is cooled, 40 ml of water are added and the solution is neutralized with solid sodium hydrogen carbonate. The separated product, which is a mixture of the two title compounds, is filtered. Thus 4.52 g (68.2%) of a crystalline product are obtained, which is recrystallized twice from isopropanol to yield pure 3-[N-methyl-N-(2-morpholino-6,7-dihydro-8H-cyclopenta[d]-1,2,4triazolo[1,5-a]pyrimidin-5-yl)aminopropylamine melting at 178°–180° C.

The mother liquors are evaporated to dryness and the residue is subjected to chromatography on a Kieselgel H column (eluent: a 1:2 mixture of benzene and ethyl acetate) to obtain N-{3-[N'-(2-morpholino-6,7-dihydro-8H-cyclopenta[d]-1,2,4-triazolo[ 1,5-a]pyrimidin-5-yl)]aminopropyl}-N-methylamine.

EXAMPLE 121

[N-(2-Methylthio-6,7-dihydro-8H-cyclopenta[d]-1,2,4-triazolo[1,5-a]pyrimidin-5-yl)]-aminoacetic acid 0.28 g (0,012 mole) of sodium metal is dissolved in 10 ml of abs. ethanol. 0.45 g (0.006 mole) of glycine and 1.45 g (0.006 mole) of 5-chloro-2-methylthio-6,7-dihydro-8H-cyclopenta[d]-1,2,4-triazolo[1,5-a]pyrimidine are added and the reaction mixture is stirred at 40° C. for 5 hours. Then it is cooled and evaporated to dryness. The residue is dissolved in 15 ml of benzene and extracted with 15 ml of water. The aqueous phase is treated with charcoal and acidified with glacial acetic acid, then the separated product is filtered and washed with water and a slight amount of isopropanol.

Yield: 1.10 g (65.6%) M.p.: 262°–267° C. (decomp.)

What we claim is:

1. A compound of Formula (I)

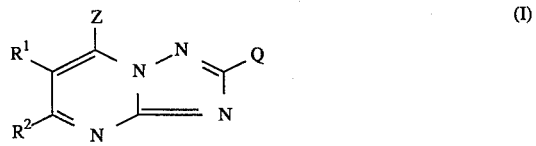

and pharmaceutically acceptable salts thereof, wherein

Q represents piperidyl, morpholinyl, or piperazinyl bonded to the triazole ring by the heterocyclic nitrogen atom and optionally carrying a $C_{1-4}$ alkyl substituent, or a group of the Formula $S(O)_pR^3$, wherein P stands for 0,1 or 2, and $R^3$ denotes straight or branched chained $C_{1-8}$ alkyl, $C_{2-6}$ alkenyl or phenyl-($C_{1-4}$ alkyl), which latter may optionally carry a halogen or a nitro substituent, or phenyl substituted by a nitro or a trifluoromethyl or a nitro and a trifluoromethyl;

or a group of the Formula $NR^4R^5$, wherein $R^4$ and $R^5$ each represent hydrogen, straight or branched $C_{1-12}$ alkyl, $C_{2-6}$ alkenyl, phenyl-($C_{1-4}$ alkyl) or di-($C_{1-4}$ alkyl)-amino-($C_{1-6}$ alkyl);

$R^1$ and $R^2$ together form a group of the Formula $(CH_2)_n$—Y—$(CH_2)_m$, wherein Y stands for a $CH_2$ group, a sulfur atom or a group of the Formula $NR^6$, where $R^6$ denotes phenyl-($C_{1-4}$ alkyl), and n is 1 or 4 and m is 1, 2, 3, 4 or 5 if Y stands for a $CH_2$ group, or n is 1 or 2 and m is 1 or 2 if Y is a $NR^6$ group, or n is 0 and m is 3 or n is 1 and m is 2 if Y is a sulfur group;

stands for a group of the Formula $NR^7R^8$ wherein $R^7$ and $R^8$ each represent hydrogen, $C_{2-6}$ alkenyl, $C_{3-8}$ cycloalkyl, adamantyl or phenyl-($C_{1-4}$ alkyl), which latter may optionally carry one to three substituent(s) selected from the group consisting of halogen, hydroxy, $C_{1-4}$ alkyl, $C_{1-4}$ alkoxy, amino and nitro; ($C_{1-4}$ alkyl)-amino-($C_{1-6}$ alkyl), di-($C_{1-4}$ alkyl)-amino-($C_{1-6}$ alkyl) or $C_{1-6}$ alkyl, which latter may optionally be substituted by a hydroxy, amino, carboxy, morpholinocarbonyl, (4-(2-hydroxy-ethyl)piperazin-1-yl)-carbonyl, ($C_{1-4}$ alkoxy)-carbonyl, piperidinyl, morpholinyl, piperazinyl, pyrrolidinyl or indol-3-yl; or $R^7$ and $R^8$ together form a group of the Formula $(CH_2)j$—W—$(CH_2)$ k, wherein j and k each represent 1, or 2 or 3, and W stands for oxygen or a $CH_2$ or CHOH group or a group of the Formula $NR^{10}$, wherein $R^{10}$ denotes hydrogen, $C_{1-4}$ alkoxycarbonyl or $C_{1-4}$ alkyl, which latter may optionally carry a substituent selected from the group consisting of hydroxy or phenyl;

or a group of the Formula $SR^9$ wherein $R^9$ stands for $C_{1-4}$ alkyl substituted by a ($C_{1-4}$ alkoxy)-carbonyl group.

2. The compound according to claim 1, wherein Q represents a ($C_{1-6}$ alkyl)-thio group or a piperidyl, morpholinyl or piperazinyl group bonded to the triazole ring by the heterocyclic nitrogen atom, $R^1$ and $R^2$ together form a group of the Formula $(CH_2)_n-Y-(CH_2)_m$, wherein n, m and Y are as defined in claim 1, Z represents morpholino or piperazino, which latter is optionally substituted by a $C_{1-4}$ alkyl) group, or Z represents a group of the Formula $NR^7R^8$, wherein $R^7$ and $R^8$ each represent straight or branched chained $C_{1-6}$ alkyl, which may optionally carry a substituent selected from hydroxy, piperidino and morpholino.

3. The compound according to claim 1, wherein said compound is
  (a) 2-(methylthio)-5-{N-(3-morpholinopropyl)}-amino-6,7,8,9-tetrahydro-1,2,4-triazolo[ 5,1-b]quinazoline;
  (b) 2-(1-methylethylthio)-5-{N-(3-morpholinopropy)}-amino-6,7,8,9-tetrahydro-1,2,4-triazolo[ 5,1-b]quinazoline;
  (c) 2-(ethylthio)-5-{N-(2-morpholinoethyl)}-amino-6,7,8,9-tetrahydro-1,2,4-triazolo[ 5,1-b]quinazoline;
  (d) 2-(methylthio)-5-[N-(2-morpholinoethyl)]amino-6,7,8,9,10,11,12,13,14,15-decahydro-cyclododeca[ d]-1,2,4-triazolo[1,5-1]pyrimidine;
  (e) 2-(methylthio)-5-[N-(2-morpholinoethyl)]amino-6,7,8,9-tetrahydro-10H-cyclohepta[ d]-1,2,4-triazolo-[1,5a]pyrimidine;
  (f) 2-(dimethylamino)-5-[N-(3-morpholinopropyl)amino-7,8-dihydro-9H-thiopyrano[3,2-d]- 1,2,4-triazolo[1,5-a]pyrimidine;
  (g) 2-(methylthio)-5-[N-(2-morpholinoethyl)]amino-6,7-dihydro-8H-cyclopenta[d]- 1,2,4-triazolo[1,5a]pyrimidine;
  (h) 2-(1-methylethylthio)-5-[N-(2-morpholino-ethyl)] amino-6,7,8,9-tetrahydro- 1,2,4-triazolo[5,1-b] quinazoline;
  (i) 2-(methylthio)-5-[N-(2-morpholinoethyl)]amino-7,8-dihydro-9H-thiopyrano[3,2-d]- 1,2,4-triazolo-[1,5a] pyrimidine;
  (j) 2-(dimethylamino)-5-[N-(2-morpholinoethyl)]amino-7,8-dihydro-9H-thiopyrano[3,2-a]- 1,2,4-triazolo-[1, 5a]pyrimidine;

and pharmaceutically acceptable salts thereof.

4. A pharmaceutical composition comprising as active ingredient a cardiotonic and/or antianginal effective amount of at least one compound according to claim 1 in admixture with suitable inert solid or liquid pharmaceutical carriers.

5. Method of cardiotonic and/or antianginal treatment, which comprises administering to a patient an effective amount of a compound of Formula (I) or a pharmaceutically acceptable salt thereof.

* * * * *

UNITED STATES PATENT AND TRADEMARK OFFICE
CERTIFICATE OF CORRECTION

PATENT NO. : 5,478,825
DATED : December 26, 1995
INVENTOR(S) : Reiter et al

It is certified that error appears in the above-indentified patent and that said Letters Patent is hereby corrected as shown below:

Title page, item
[75] Please change "Nagyoros" to --Nagykoros--; change "Peocz" to --Petocz--; change "Hegeus" to --Hegedus--; change "EnioSzirt" to --Eniko Szirt--; and change "Csoro" to --Csorgo--.

Signed and Sealed this

Fourth Day of June, 1996

Attest:

BRUCE LEHMAN

*Attesting Officer*    *Commissioner of Patents and Trademarks*